United States Patent [19]
Springer et al.

[11] Patent Number: 6,025,340
[45] Date of Patent: Feb. 15, 2000

[54] SURFACE EXPRESSION OF ENZYME IN GENE DIRECTED PRODRUG THERAPY

[75] Inventors: Caroline Joy Springer, Sutton; Richard Marais, London, both of United Kingdom

[73] Assignee: Cancer Research Campaign Technology Limited, London, United Kingdom

[21] Appl. No.: 08/776,251

[22] PCT Filed: Jul. 27, 1995

[86] PCT No.: PCT/GB95/01782

§ 371 Date: Jan. 31, 1997

§ 102(e) Date: Jan. 31, 1997

[87] PCT Pub. No.: WO96/03515

PCT Pub. Date: Feb. 8, 1996

[30] Foreign Application Priority Data

Jul. 27, 1994 [GB] United Kingdom .................... 9415167

[51] Int. Cl.[7] .................................................... A01N 43/04
[52] U.S. Cl. .......................... 514/44; 435/69.1; 435/69.7; 435/69.8; 435/320.1; 435/325; 435/455; 536/23.2; 536/23.4; 536/23.7; 536/24.1; 424/94.1; 424/94.63
[58] Field of Search .......................... 514/44; 435/320.1, 435/375, 172.1, 172.3, 69.1, 69.7, 69.8, 212, 220; 536/23.2, 23.4, 23.7, 24.1; 424/94.1, 94.63; 935/52, 62, 66, 48, 51, 455

[56] References Cited

U.S. PATENT DOCUMENTS

| | | | |
|---|---|---|---|
| 4,935,352 | 6/1990 | Koichi et al. | 435/69.52 |
| 4,975,278 | 12/1990 | Senter et al. | 424/94.3 |
| 5,223,408 | 6/1993 | Goeddel et al. | 435/69.3 |
| 5,405,990 | 4/1995 | Burke et al. | 560/134 |

FOREIGN PATENT DOCUMENTS

WO 96/16179  5/1996  WIPO .

OTHER PUBLICATIONS

Bakir et al The Journal of Nuclear Medicine 33 (12) 2154–2160 Dec. 1992,.
Allan et al Br. J. Cancer (1993) 67:706–712.
Eccles et al Cancer Research (Oct. 1, 1994) 54: 5171–5177.
Darnell et al. (Molecular Biology, Scientific American Books,, Inc., 1990, pp. 657–678,.
Vijaya et al. reference (Mol. Cell. Biol. (1988), 8(4), 1709–14).
Denzer et al. reference (Embo Journal, (Dec. 15, 1995) 14 (24) 6311–7).
Stein et al. (Mol. Cell Biol. 14(5):3392–3402, 1994).
Kreitman et al. (P.N.A.S., vol. 91, pp. 6889–6893, 1994).
Ngo et al., in: The Protein Folding Problem and Tertiary Structure Prediction, 1994, Merz et al., (ed.), Birkhauser, Boston, MA, pp. 433 and 492–495).
Guan et al. (Cell, (Jul. 1984) 37 (3) 779–87).
Mastrangelo et al. (Seminars in Oncology, vol. 23, No. 1:4–21, 1996).
Gunzburg et al., Molecular Medicine Today, pp. 410–417, 1995.
Ledley (Human Gene Ther. (1995) 6:1129–1144).
Melton et al. (J. Natl. Cancer Inst., 88 (3/4):153–165, 1996,.
Deonarain et al. (British J. Cancer, 70 (5):786–94), 1994).
Springer et al. (Anti Cancer Design, 10:361–372), 1995.
T. Friedmann Sci. Amer. pp. 96–101, Jun. 1997.
S. Orkin et al. NIH Report on Gene Therapy, Dec. 1995.
J. Winther et al. Eur. J. Biochem. 197: 681–9, 1991.
Y. Dobashi et al. Oncogene 6: 1151–9, 1991.
M. McMahon et al. Mol. Cell Biol. 11(9) 4760–70, 1991.
J. Watson et al., Mol. Biol. of the Gene, 4th Ed. Benjamin/Cummings, NJ, pp. 612–614, 1987.
B. Alberts et al. Mol. Biol. of the Cell, Garland Publ., Inc. NY pp. 341–349, 1983.

*Primary Examiner*—Bruce R. Campell
*Assistant Examiner*—Dave Trong Nguyen
*Attorney, Agent, or Firm*—Nixon & Vanderhye, P.C.

[57] ABSTRACT

The invention provides a two component system for use in association with one another comprising:
(a) a vector capable of expressing an enzyme at the surface of a cell; and
(b) a prodrug which can be converted into an active drug by said enzyme, useful in the treatment of tumours.

23 Claims, 13 Drawing Sheets

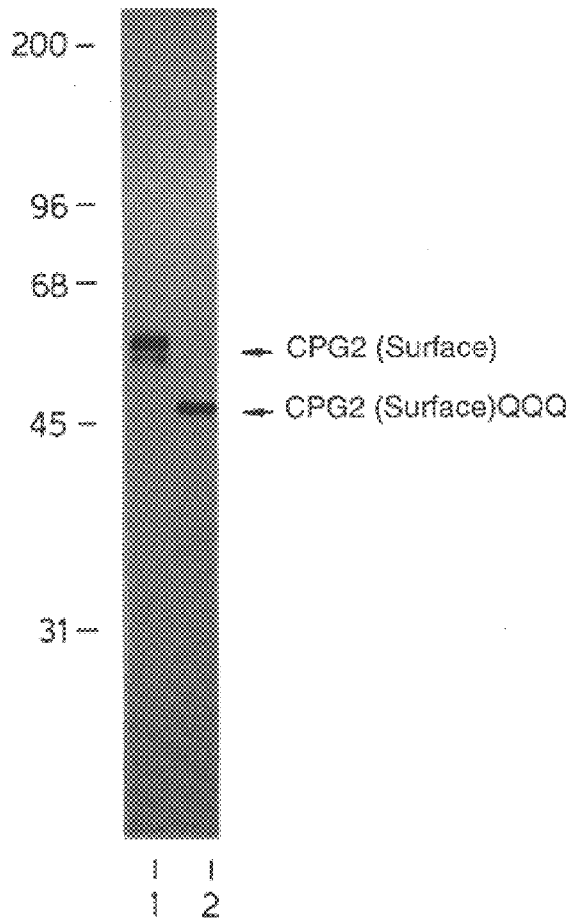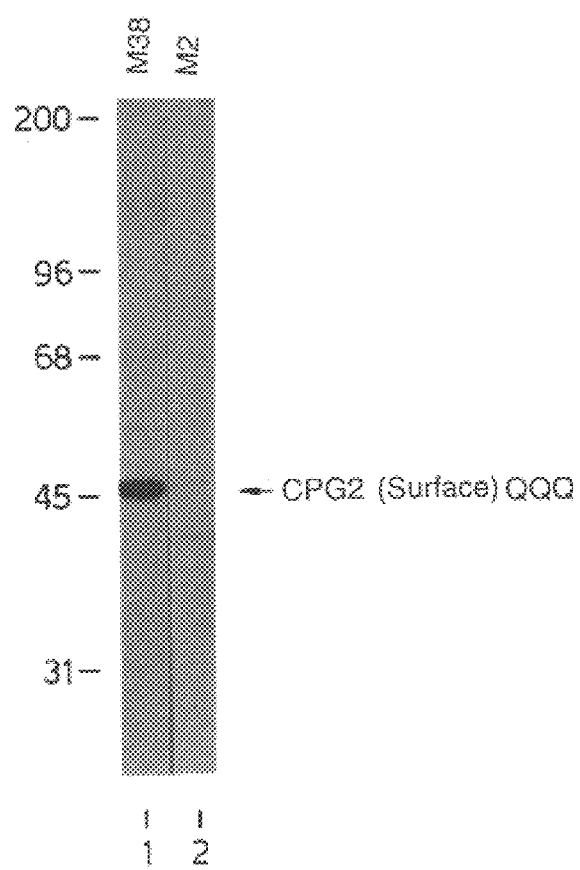

□  0 % OF CELLS EXPRESSING CPG2 (Surface) QQQ

■  10 % OF CELLS EXPRESSING CPG2 (Surface) QQQ

○  100 % OF CELLS EXPRESSING CPG2 (Surface) QQQ

SURFACE EXPRESSION OF ENZYME IN GENE DIRECTED PRODRUG THERAPY

This application is the U.S. national phase of PCT application PCT/GB95/01782 filed Jul. 27, 1995 with a claim to the priority of U.K. application 9415167.7 filed Jul. 27, 1994.

INTRODUCTION AND BACKGROUND TO THE INVENTION

The present invention relates to gene directed enzyme prodrug therapy (GDEPT) and its use in the treatment of disease, including tumours.

A therapeutic approach termed "virus-directed enzyme prodrug therapy" (VDEPT) has been proposed as a method for treating tumour cells in patients using prodrugs. Tumour cells are targeted with a viral vector carrying a gene encoding an enzyme capable of activating a prodrug. The gene may be transcriptionally regulated by tissue specific promoter or enhancer sequences. The viral vector enters tumour cells and expresses the enzyme, in order that a prodrug is converted to an active drug within the tumour cells (Huber et al, Proc. Natl. Acad. Sci. USA (1991) 88, 8039). Alternatively, non-viral methods for the delivery of genes have been used. Such methods include calcium phosphate co-precipitation, microinjection, liposomes, direct DNA uptake, and receptor-mediated DNA transfer. These are reviewed in Morgan & French Anderson, Annu. Rev. Biochem., 1993,62;191. The term "GDEPT" (gene-directed enzyme prodrug therapy) is used to include both viral and non-viral delivery systems.

The success of a GDEPT system relies upon two limiting factors. The system requires cells which need to be targeted by the vector to be infected. If a cell does not become infected then no active drug will be produced within it so that in order to be killed active drug will need to enter it by a bystander effect, having been produced in another infected cell. Not all active drugs when produced inside a cell will be capable of leaving that cell in order to do this. Further, it is a requirement that the prodrug enters the cell. Some prodrugs may not be capable of crossing the membrane of a cell.

DISCLOSURE OF THE INVENTION

In order to overcome these problems, the present invention provides a two component system for use in association with one another comprising:

(a) a vector capable of expressing an enzyme at the surface of a cell; and (b) a prodrug which can be converted into an active drug by said enzyme.

The vector may be a RNA or DNA vector. It may be derived from a viral vector, including any suitable vector available in the art for targeting tumour cells.

The invention also provides the system of the invention for use in a method of treatment of a patient, and a method of treating a tumour in a patient in need of treatment which comprises administering to said patient an effective amount of a vector encoding an enzyme capable of being expressed on the surface of a cell and a prodrug capable of being converted by said enzyme to an active drug.

BRIEF DESCRIPTION OF THE DRAWINGS

FIG. 3. Effect of glycosylation mutations on expressed CPG2(surface)

FIG. 4. Effect of mutating all the potential glycosylation sites in CPG2(surface)

FIG. 6.

FIG. 9. FIG. 9A shows (A) immunoblot analysis: transient expression of CPG2(surface) and CPG2(surface)QQQ in NIH3T3 cells. The position of migration of CPG2(surface) and CPG2(surface)QQQ is indicated, as is the position of migration of the standard molecular mass markers (in kDa), to the left of the figure.

FIG. 10. FIG. 10A shows (A) immunoblot analysis: constitutive expression of CPG2(surface)QQQ in MDA MB 361 cells. The position of migration of CPG2(surface)QQQ is indicated as is the position of migration of the standard molecular mass markers (in kDa), to the left of the figure.

FIG. 11.

DETAILED DESCRIPTION OF THE INVENTION

A. Vector systems

Figure 1:
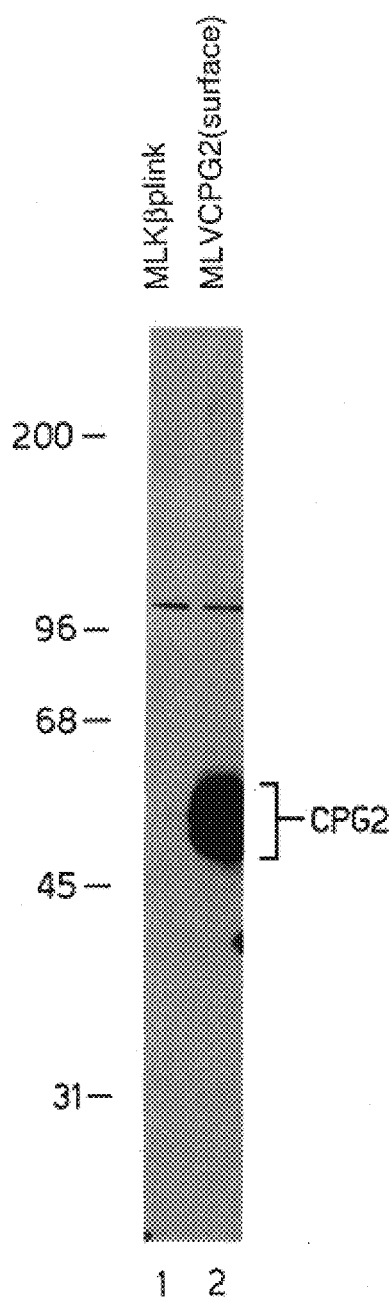
FIG. 1. Expression of CPG2(surface) in NIH3T3 cells NIH3T3 cells were transfected with MLVβplink (lane 1) or with MLVCPG2(surface) (lane 2). The cells were extracted into buffer A and samples of each were electrophoresed in 10% w/v polyacrylamide gels, transferred to nitrocellulose and probed with a CPG2 specific polyclonal antibody. The position of migration of CPG2(surface) is shown and the positions of migration of standard molecular mass markers (in kDa) are shown to the left of the figure FIG. 2. Effect of tunicamycin on the expression of CPG2 (surface) in NIH3T3 cells

Examples of suitable vector systems include vectors based on the Molony murine leukaemia virus are known (Ram, Z et al, Cancer Research (1993) 53;83–88; Dalton & Treisman, Cell (1992) 68; 597–612). These vectors contain the Murine Leukaemia virus (MLV) enhancer cloned upstream at a β-globin minimal promoter. The β-globin 5' untranslated region up to the initiation ATG is supplied to direct efficient translation of the cloned protein. The initiator ATG straddles an NcoI restriction site and thus can be used to clone a protein coding sequence into the vector. This vector further contains a polylinker to facilitate cloning, followed by the β-globin 3'-untranslated region and polyadenylation sites. The MLV enhancer is of particular use since it is a strong enhancer and is active in most murine and human cell lines.

Suitable viral vectors further include those which are based upon a retrovirus. Such vectors are widely available in the art. Huber et al (ibid) report the use of amphotropic retroviruses for the transformation of hepatoma, breast, colon or skin cells. Culver et al (Science (1992) 256; 1550–1552) also describe the use of retroviral vectors in GDEPT. Such vectors or vectors derived from such vectors may also be used. Other retroviruses may also be used to make vectors suitable for use in the present invention. Such retroviruses include rous sarcoma virus (RSV). The promoters from such viruses may be used in vectors in a manner analogous to that described above for MLV.

Englehardt et al (Nature Genetics (1993) 4; 27–34) describe the use of adenovirus based vectors in the delivery of the cystic fibrosis transmembrane conductance product (CFTR) into cells, and such adenovirus based vectors may also be used. Vectors utilising adenovirus promoter and other control sequences may be of use in delivering a system according to the invention to cells in the lung, and hence useful in treating lung tumours.

In general, the vector may be any DNA or RNA vector used in VDEPT or GDEPT therapies.

B. Enzymes

The enzyme may be any enzyme which is not normally expressed on the surface of a cell, nor released into the circulation, particularly a mammalian (especially human) cell, and which is capable of converting a prodrug into an active drug. The enzyme may be a mammalian enzyme which does not naturally occur in a human or a human enzyme which is not normally accessible to the prodrug. This includes enzymes from other species as well as mammalian enzymes which are altered in a manner which is selective for the prodrug. In other words, the alteration means that the conversion of the prodrug to an active drug by the natural enzyme will be at a rate one or more orders of magnitude less than the rate at which the altered enzyme operates. Altered enzymes may be made by standard recombinant DNA techniques, e.g. by cloning the enzyme, determining its gene sequence and altering the gene sequence by methods such as site-directed mutagenesis.

The enzyme will usually convert the prodrug into an active drug by removing a protecting group from the prodrug. In most cases, the protecting group will be cleaved as a whole from the prodrug. However, it is also possible for the enzyme to cleave or simply alter part of the protecting group, resulting in a partially cleaved or altered protecting group which is unstable, resulting in spontaneous removal of the remainder of the group. Such prodrugs are of particular use in association with the nitroreductase enzyme described below.

Preferably, the enzyme is a non-mammalian enzyme. Suitable non-mammalian enzymes include bacterial enzymes. Bacterial enzymes include carboxypeptidases, such as carboxypeptidase G2 (CPG2), as disclosed in WO88/07378, *Pseudomonas* γ-glutamylhydrolase EC3.4.22.12 (Levy C. C. & Goldstein P. J. Biol. Chem. 242; p2933 (1967)) and nitroreductases, such as an *E. coli* nitroreductase as disclosed in WO93/08288. Examples of other suitable enzymes include thymidine kinase (tk), especially viral tk such as VZV or HSV tk; and β-lactamase and β-glucoronidase. Other enzymes include penicillin V amidase, penicillin G amidase and cytosine deaminase.

Enzymes expressed in a vector system of the present invention will generally undergo processing through the Golgi apparatus and endoplasmic reticulum to reach the surface of the cells. N-linked glycosylation occurs in the Golgi apparatus and endoplasmic reticulum at a motif whose primary amino acid sequence is Asn-Xaa-Ser/Thr (where Xaa is any amino acid); the glycosylation occurs on the Asn residue. In some cases, this can lead to a reduction in activity of the enzyme compared to its unglycosylated native form. It is thus desirable that vectors of the present invention are altered to change by substitution, deletion or insertion at one or more glycosylation sites.

For example, within the primary amino acid sequence of CPG2, there are three such consensus motifs, located at residues Asn 22, Asn 264 and Asn 272. Alteration of one or more of these sites is preferred when CPG2 is used in the present invention. Desirably, the alteration is substitution to leucine or glutamine.

In general, alterations to enzymes which are amino acid substitutions of from at least 1 to all glycosylation sites are particularly preferred, although deletions or insertions of for example 1, 2, 3, 4, 5 or more amino acids are also possible. In any event, the alteration will be such that the enzyme retains its ability to convert a prodrug to an active drug at substantially the same rate as the unchanged, unglycosylated enzyme. In this context, "substantially unchanged" will desirably be within 1 order of magnitute, and preferably from about 2-fold less to 2, 5 or 10 fold more.

In addition to specific changes the enzyme may otherwise be altered by truncation, substitution, deletion or insertion as long as the activity of the enzyme is substantially unchanged as defined above. For example, small truncations in the N- and/or C-terminal sequence may occur as a result of the manipulations required to produce a vector in which a nucleic acid sequence encoding the enzyme is linked to the various other signal sequences described herein. The activity of the altered enzyme may be measured in model systems such as those described in the examples.

An example of a truncated enzyme is CPG2* which contains amino acids 23 to 415 of SEQ ID NO: 1.

In a further aspect of the present invention, there is provided a vector comprising a bacterial carboxypeptidase which has been altered by substitution, deletion or insertion at one or more glycosylation sites. The carboxypeptidase is desirably CPG2 with the amino acid sequence of SEQ ID NO: 1 except for said one or more substitutions, deletions or insertions. Variants of such carboxypeptidases containing further substitutions, deletions or insertions but which retain substantially unchanged carboxy-peptidase activity are a further part of this aspect of the invention. Such variants may for example include truncated enzymes as discussed above.

The invention also provides a nucleic acid which may be RNA or DNA encoding such carboxypeptidases, and vectors, including vectors, comprising such a nucleic acid. The nucleic acid is preferably that of SEQ ID NO: 1 (except where altered to remove one or more glycosylation sites), or a fragment thereof encoding the abovementioned variants of carboxypeptidase. The vector may be an expression vector, wherein said nucleic acid is operably linked to a promoter compatible with a host cell. The invention thus also provides a host cell which contains an expression vector of the invention. The host cell may be bacterial (e.g. *E.coli*), insect, yeast or mammalian (e.g. hamster or human).

Host cells of the invention may be used in a method of making a carboxypeptidase enzyme or fragment thereof as defined above which comprises culturing the host cell under conditions in which said enzyme or fragment thereof is expressed, and recovering the enzyme or fragment thereof in substantially isolated form. The enzyme or fragment thereof may be expressed as a fusion protein.

C. Other vector components

In the system according to the invention the enzyme may be linked to a signal sequence which directs the enzyme to the surface of a mammalian cell. This will usually be a mammalian signal sequence or a derivative thereof which retains the ability to direct the enzyme to the cell surface. This will be needed unless the enzyme has an endogenous signal sequence which does this. Even if an enzyme does have such a signal sequence, it can be replaced by another signal sequence where this is desirable or appropriate. Suitable signal sequences include those found in transmembrane receptor tyrosine kinases such as the c-erbB2 (HER2/neu) signal sequence or variants thereof which retain the ability to direct expression of the enzyme at the cell surface. The c-erbB2signal sequence can be obtained by reference to Coussens et al (1985) Science 230; 1132–1139.

The experiments described in the Examples herein may be used to determine variants of this, or other signal sequences, for their ability to express the enzyme at the cell surface. The variants may be produced using standard techniques known as such in molecular biology, eg. site-directed mutagenesis of a vector containing the signal sequence.

Further suitable signal sequences include those which may be found in the review by von Heijne (1985) J. Mol. Biol. 184; 99–105.

The enzyme of the system according to the invention will be expressed at the surface of a cell. This means that it will be expressed in such a fashion as to have the enzyme exposed outside the cell so that it may interact with the prodrug, but will still be attached to the plasma membrane by virtue of a suitable plasma membrane-anchor. A suitable anchor will be a polypeptide anchor which is expressed by the vector. For example, the enzyme which is linked to a sequence which is a transmembrane region which anchors the enzyme in the membrane of the cell. Such a transmembrane region can be derived from transmembrane receptor kinases, such as c-erbB2, EGF receptors and CSF-1 receptors. The c-erbB2 transmembrane region is set out in the example below. Variants of such transmembrane regions may also be used provided that they retain the ability to anchor the enzyme in the membrane of a cell, such that the active portion of the enzyme is outside the cell, and at its surface other anchors eg. Peptidoglycan anchors are lipid anchors and could also possibly be used.

The anchor such as the one from a the transmembrane region is attached to the open reading frame of the enzyme gene by suitable molecular biology techniques. When the protein is expressed it will have the anchor attached as the enzyme/anchor fusion protein is made. The anchor will then embed into the membrane and will hold the enzyme there.

Vectors encoding the enzyme, together with, when required, a signal sequence and/or transmembrane region may be made using recombinant DNA techniques known per se in the art. The sequences encoding the enzyme, signal sequence and transmembrane regions may be constructed by splicing synthetic or recombinant nucleic acid sequences together, or modifying existing sequences by techniques such as site directed mutagenesis. Reference may be made to "Molecular Cloning" by Sambrook et al (1989, Cold Spring Harbor) for discussion of standard recombinant DNA techniques.

D. Promoters

The enzyme will be expressed in the vector using a promoter capable of being expressed in the cell to which the vector is targeted. The promoter will be operably linked to the sequences encoding the enzyme and its associated sequences. For example, the c-erbB2 proto-oncogene is expressed in breast tissues at low levels and in a tissue restricted manner. In some tumour states however the expression of this protein is increased, due to enhanced transcriptional activity. Notable examples of this are breast tissue (about 30% of tumours), ovarian (about 20%) and pancreatic tumours (about 50–75%). In such tumours where expression of c-erbB2 is increased due to enhanced transcription or translation, the c-erbB2 promoter may be used to direct expression of proteins in a cell specific manner.

With the GDEPT system of the present invention utilising c-erbB2 promoters to target such tumours, the specificity of GDEPT is increased since transfection of normal cells by a vector with a c-erbB2 promoter will provide only limited amount of enzyme levels and thus limited activation of prodrug.

The c-erbB-2 promoter has been sequenced to −1500 and may be obtained by reference to Hudson et al, (1990) J. Biol. Chem. 265; 4389–4393. The major start site of transcription has been determined by Ishii et al (1987) Proc. Natl. Acad. Sci. 84; 4374–4378 and Tal et al (1987) Mol. Cell Biol. 7; 2597–2601. This start site is referred to as +1 and this numbering is referred to herein. Translation of c-erbB-2 starts at +178. The promoter has a CAAT box at −75 and a TATA box at −25.

Hollywood and Hurst (1993) EMBO J. 12; 2369–2375 report that in mammary cells, regions of the promoter at −100 and −213 are important for the regulation of transcription. (see also Sarkar et al (1994) J. Biol. Chem. 269; 12285–12289).

In order to achieve expression from a vector utilizing the c-erbB-2 promoter, it is desirable to use the c-erbB-2 promoter region from the CAAT box, and preferably the TATA box, upstream to include sequence elements responsible for specificity of expression in particular tissues, such as those found for mammary cells by Hollywood and Hurst (ibid). The promoter will thus desirably include at least all the nucleotides upstream (5') of the CAAT box to about the 250th, eg. 300th, 400th, 500th, 600th, 700th, 800th, 900th or further nucleotide 5' to the start of transcription. It is also preferred to include the TATA box. Optionally, the c-erbB-2 sequences downstream of the TATA box to the start of translation at +178 may also be used.

Although the human c-erbB-2 promoter sequence is preferred, modified promoter sequences which are capable of selectively hybridizing to the human sequence may also be used. A promoter sequence capable of selectively hybridizing to the human promoter sequence will be generally at least 70%, preferably at least 80 or 90% and more preferably at least 95% homologous to the promoter region or fragment thereof over a region of at least 20, preferably at least 30, for instance 40, 60 or 100 or more contiguous nucleotides.

In general, those of skill in the art will appreciate that some regions of the promoter such as those at −213 will need to be retained to ensure tumour specificity of expression from the vector whereas other regions of the promoter may be modified or deleted without significant loss of specificity. Thus, modified promoters which are transcriptionally regulated substantially to the same degree as human c-erbB-2 are preferred. The degree of regulation of such candidate promoters can be tested and assessed by those of skill in the art using for example CAT assays in accordance with those described by Hollywood and Hurst (ibid).

"Operably linked" refers to a juxtaposition wherein the promoter and the enzyme-coding sequence are in a relationship permitting the coding sequence to be expressed under the control of the promoter. Thus, there may be elements such as 5' non-coding sequence between the promoter and coding sequence which is not native to either the promoter nor the coding sequence. Such sequences can be included in the vector if they do not impair the correct control of the coding sequence by the promoter.

Other suitable promoters include viral promoters such as mammalian retrovirus or DNA virus promoters. Suitable promoters include those used in vectors described above, e.g. MLV, CMV, RSV and adenovirus promoters. Preferred adenovirus promoters are the adenovirus early gene promoters. Strong mammalian promoters may also be suitable. An example of such a promoter is the EF-1α promoter which may be obtained by reference to Mizushima and Nagata ((1990), Nucl. Acids Res. 18; 5322). Variants of such promoters retaining substantially similar transcriptional activities may also be used.

Vectors which comprise the c-erbB-2 promoter form a further novel aspect of the present invention and may be used in systems in which the vector expresses a gene capable of converting a prodrug into an active drug within a target cell. Thus the invention provides a viral vector comprising a c-erbB-2 promoter operably linked to a gene encoding an enzyme, the enzyme being capable of converting a prodrug into an active drug. The invention also provides a kit which comprises a vector as defined above together with a prodrug which is capable of being converted to an active drug by the enzyme encoded by the vector. In another aspect, the invention provides a vector as defined above or a kit as defined above for use in a method of treatment of the human or animal body, and in particular a method of treatment of tumours in which the c-erbB-2 proto-oncogene is overexpressed. In a further aspect, the invention provides a method of treatment of tumours, and in particular a method of treatment of tumours in which the c-erbB-2 proto-oncogene is overexpressed, which method comprises administering to an individual with a tumour (i) an effective amount of a vector as defined above, and (ii) an effective amount of a prodrug capable of being converted to an active drug by the enzyme encoded by the vector.

E. Prodrugs

The prodrug for use in the system will be selected to be compatible with the enzyme, ie. such that the enzyme will be capable of converting the prodrug into an active drug. Desirably, the toxicity of the prodrug to the patient being treated will be at least one order of magnitude less toxic to the patient than the active drug. Preferably, the active drug will be several, eg 2, 3, 4 or more orders of magnitude more toxic. Suitable prodrugs include nitrogen mustard prodrugs and other compounds such as those described in WO88/07378, WO89/10140, WO90/02729, WO91/03460, EP-A-540 263, WO94/02450, WO95/02420 or WO95/03830 which are incorporated herein by reference.

E(i)—Nitrogen mustard prodrugs

Nitrogen mustard prodrugs include compounds of the formula:

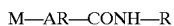

where Ar represents an optionally substituted ring aromatic ring system, R—NH is the residue of an α-amino acid R—NH₂ or oligopeptide R—NH₂ and contains at least one carboxylic acid group, and M represents a nitrogen mustard group.

The residue of the amino acid R—NH is preferably the residue of glutamic acid. It is disclosed in WO88/07378 that the enzyme carboxypeptidase G2 is capable of removing the glutamic acid moiety from compounds of the type shown above, and the removal of the glutamic acid moiety results in the production of an active nitrogen mustard drug.

Thus nitrogen mustard prodrugs of use in the invention include the prodrugs of generic formula I of WO94/02450 and salts thereof, and in particular those of formula (I):

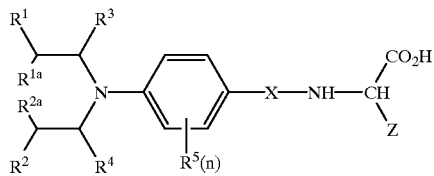

(I)

wherein $R^1$ and $R^2$ each independently represent chlorine, bromine, iodine, $OSO_2Me$, $OSO_2phenyl$ (wherein phenyl is optionally substituted with 1,2,3,4 or 5 substituents independently selected from $C_{1-4}$alkyl, halogen, —CN or $NO_2$);
$R^{1a}$ and $R^{2a}$ each independently represents hydrogen, $C_{1-4}$ alkyl or $C_{1-4}$ haloalkyl;
$R^3$ and $R^4$ each independently represents hydrogen, $C_{1-4}$ alkyl or $C_{1-4}$ haloalkyl;
n is an integer from 0 to 4;
each $R^5$ independently represents hydrogen, $C_{1-4}$ alkyl optionally containing one double bond or one triple bond, $C_{1-4}$ alkoxy, halogen, cyano, —NH₂, —CONR⁷R⁸ (wherein $R^7$ and $R^8$ are independently hydrogen, $C_{1-6}$ alkyl or $C_{3-6}$ cycloalkyl) or two adjacent $R^5$ groups together represent
a) C4 alkylene optionally having one double bond;
b) C3 alkylene; or
c) —CH=CH—CH=CH—, —CH—CH—CH2— or —CH2—CH=CH— each optionally substituted with 1, 2, 3 or 4 substituents said substituents each independently selected from the group consisting of $C_{1-4}$ alkyl, $C_{1-4}$ alkoxy, halogen, cyano and nitro;
X is a group —C(O)—, —O—C(O)—, —NH—C(O)— or —CH₂—C(O)—; and
Z is a group —CH₂—T—C(O)—OR⁶ where T is CH₂, —O—, —S—, —(SO)— or —(SO₂)—, and $R^6$ is hydrogen, $C_{1-6}$ alkyl, $C_{3-6}$ cycloalkyl amino, mono-di—$C_{1-6}$ alkylamino or mono or $diC_{3-6}$ cycloalkyl amino, provided that when $R^6$ is hydrogen T is —CH₂—; and physiologically acceptable derivatives, including salts, of the compounds of formula (I).

Halogen includes fluorine, chlorine, bromine and iodine. Preferred values for the groups $R^{1a}$ and $R^{2a}$ are methyl and hydrogen, especially hydrogen. Preferred values for the groups $R^3$ and $R^4$ are hydrogen, methyl and trifluoromethyl, especially hydrogen. Preferred values for the groups $R^1$ and $R^2$ are I, Br, Cl, $OSO_2Me$ and $OSO_2phenyl$ wherein phenyl is substituted with one or two substituents in the 2 and/or 4 positions. I, Cl and $OSO_2Me$ are especially preferred.

Preferred values for $R^5$ when n is an integer from 1 to 4 are fluorine, chlorine, methyl-CONH₂ and cyano.

Preferably, n is 0, 1 or 2. When n is 1 or 2 it is preferred that $R^5$ is fluorine at the 3 and/or 5 positions of the ring. The group X is preferably —C(O)—, —O—C(O)— or —NH—C(O)—. Z is preferably a group —CH₂CH₂—COOH.

Preferred specific compounds include:

N-4-[(2-chloroethyl)(2-mesyloxyethyl)amino]benzoyl-L-glutamic acid (referred to below as "CMDA") and salts thereof;

N-(4-[bis(2-chloroethyl) amino]-3-fluorophenylcarbamoyl)-L-glutamic acid and salts thereof;

N-(4-[bis(2-chloroethyl) amino]phenylcarbamoyl)-L-glutamic acid and salts thereof;

N-(4-[bis(2-chloroethyl) amino]phenoxycarbonyl)-L-glutamic acid and salts thereof; and N-(4-[bis(2-iodoethyl)amino]phenoxycarbonyl)-L-glutamic acid (referred to below as "prodrug 2") and salts thereof.

Particular sub-groups of the compounds of the present invention of interest may be obtained by taking any one of the above mentioned particular or generic definitions for $R^1$–$R^4$, $R^5$, X or W either singly or in combination with any other particular or generic definition for $R^1$–$R^4$, $R^5$, X or W.

Other prodrugs include compounds of the formula (II):

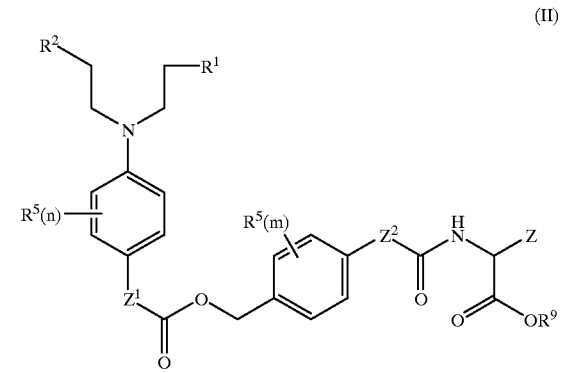

(II)

wherein $R^1$, $R^2$, $R^5$, n and Z are as defined for compounds of the formula (I) above;

m is an integer from 0 to 4,
$Z^1$ and $Z^2$ are each independently —O— or —NH—; and
$R^9$ is hydrogen, t-butyl or allyl;
and physiologically acceptable derivatives of the compound of formula (I). Preferred values of $R^1$, $R^2$, $R^5$, n and Z are as defined above for compounds of the formula (I). Preferred values of m are 0, 1 or 2 as defined for n above. $R^9$ is preferably hydrogen, but can be protected especially during synthesis by groups such as allyl or t-butyl.

These prodrugs can be activated at the site of a tumour by a carboxypeptidase enzyme, for example, CPG2 as disclosed in WO88/07378 or WO94/02450.

Nitrogen mustard prodrugs of the formula (III):

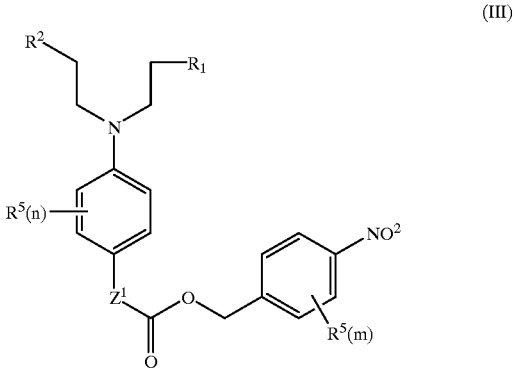

(III)

wherein $R^1$, $R^2$, $R^5$, $Z^1$, n, and m are as defined for compounds of the formula (II), and physiologically acceptable derivatives thereof, may also be used in the present invention.

These prodrugs can be activated at the site of a tumour by a nitroreductase enzyme, for example, as disclosed in WO93/08288.

Usually to ensure enzyme activity a cofactor such as riboside or a ribotide of nicotinic acid or nicotinamide will be required and may be administered with the prodrug.

Compounds of the formulae (II) and (III) may be made using reactions and methods known per se in the art of chemistry. The following methods are of particular use:

A: Compounds of formula (II) where $Z^1$ is —O—:

Compounds of the formula (I) in which $Z^1$ is —O— may be made by reacting a nitrogen mustard of formula (IV)

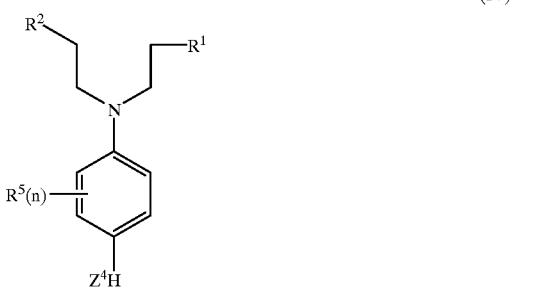

(IV)

where $R^1$, $R^2$, and $R^5$ and n are as defined above and $Z^4$ is —O— with a linker of formula (V)

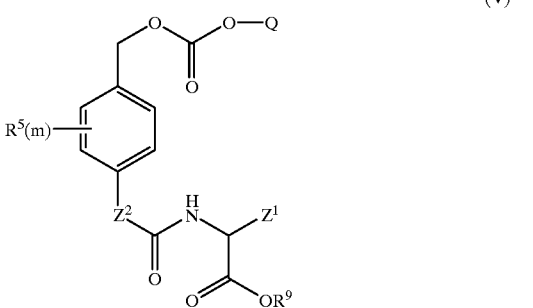

(V)

where $R^5$, m, $Z^2$, $R^9$ and $Z^3$ are as defined above, and Q is hydrogen or a leaving group. This reaction may be done in aprotic solvents in the presence of a base, for example DMF and triethylamine.

Preferred leaving groups Q include a succinimidyl group, a 4-nitrophenyl carbonate group, a pentafluorophenyl carbonate and a tetrachloroethyl group $CH(Cl)CCl_3$.

(ii) Compounds of the formula (IV) may be made starting from 4-nitrophenol optionally substituted with the group(s) $R^5_{(n)}$ (as defined above). The phenolic group is protected as an adamantanyloxycarbonyl-derivative (by reacting the starting materials with adamantanyl-fluoroformate and triethylamine in THF at rt). The protected 4-nitrophenyl carbonate is reduced to the corresponding amine by hydrogen transfer in ethanol using ammonium formate and Pd/C 10% as catalyst at room temperature. The amine is then hydroxyethylated with ethylene oxide in AcOH at 20° C. and then reacted to the desired nitrogen mustard. Reference may be made to EP-A-433 360 or EP-A-490970 for suitable conditions. The compounds may be purified by column chromatography. Deprotection to remove the adamantyl group may be carried out in trifluoroacetic acid.

(iii) Alternatively, the nitrogen mustard of formula (IV) may be activated as a chloroformate by treatment with phosgene or triphosgene in an aprotic solvent and triethylamine followed by coupling with a compound of formula (VI):

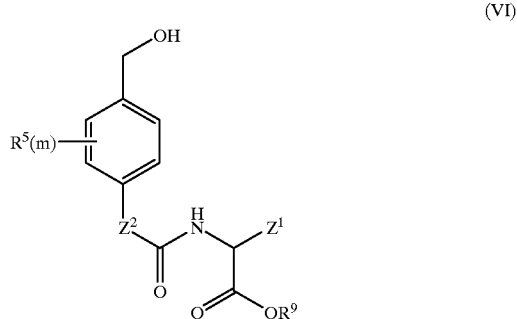

(VI)

where $R^5$, m, $Z^2$, $R^9$ and $Z^1$ are as defined above. This may be carried out in THF or other aprotic solvents in the present of a base (for example triethylamine or pyridine).

(iv) A further alternative route of synthesis of compounds of the formula (II) in which $Z^1$ is —O— involves direct coupling of 4-nitrophenol optionally substituted with the group(s) $R^5_{(n)}$ (as defined above) with the compound of the formula (V) or by reaction of the said optionally substituted 4-nitrophenol compound chlorofromate with the compound of formula (V), followed in each case by the reaction described above to convert the nitro group, via an amine, to a mustard group.

B: Compounds of formula (II) where $Z^1$ is —NH—:

(i) Compounds of the formula (II) in which $Z^1$ is —NH— may be made by reaction of a compound of formula (IV) in which $Z^4$ is —NH— with a linker of the formula (V) in aprotic solvents and in the presence of a base. Compounds of the formula (IV) in which $Z^4$ is —NH— may be made from a 1-halo-4-nitrobenzy compound, optionally substituted with the group(s) $R^5_{(n)}$ (as defined above). This is converted to the corresponding 1-bis-hydroxyethylamino-4-nitro-benzyl compound by reaction with diethanolamine with heat and the resulting product purified by column chromatography. The corresponding 4-nitro nitrogen mustard may be made by for example mesylation using mesyl chloride in pyridine and subsequent reaction to other halo mustards, e.g. bromo or iodo mustards if required. The 4-nitro group may be reduced by hydrogen transfer in ethanol using ammonium formate and a Pd/C 10% catalyst at 20° C.

(ii) Alternatively the 1-bis-hydroxyethylamino-4-nitrobenzyl compound mentioned above can be reduced using ammonium formate and Pd/C 10% as catalyst in ethanol at 20° C. to provide the corresponding phenylenediamino derivative. This derivative can be converted into the corresponding 4-amino nitrogen mustard as described in the above paragraph, e.g. initially by reaction with mesyl chloride.

C: Compounds of formula (III):

(i) Compounds of the formula (III) may be obtained by coupling nitrogen mustard phenol compounds described in section A(i) above with 4-nitrobenzyl choloroformate optionally substituted with the group(s) $R^5_{(m)}$ (as defined above) in the presence or absence of triethylamine at 20° C.

(ii) Alternatively aniline nitrogen mustards as described in section B(ii) above may be used with the chloroformated as described in section C(i) above.

D: Compounds of the formula (IV) in which $Z^2$ is —NH—:

(i) Compounds of the formula (IV) in which $Z^2$ is —NH— may be made from a 4-nitro benzylic alcohol optionally substituted with the group(s) $R^5_{(n)}$ (as defined above). The hydroxyl function is protected as a pyranyl- or t-butyl-dimethylsilyl (TBDMSi)-ether by treatment at 20° C. with 3,4-2H-dihydropyran and pyridinium-p-toluensulfonate (PPTS) in an aprotic solvent or with TBDMSi chloride and imidazole in dimethylformamide (DMAC), respectively. The intermediate thus obtained is reduced to the corresponding amine by hydrogen transfer in ethanol using ammonium formate and Pd/C 10% as catalyst at 20° C. This amine is converted to a glutamyl ester intermediate of formula (VII):

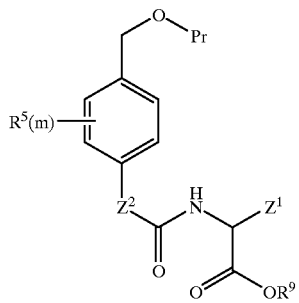

(VII)

where $R^5$, m, $R^9$ and $Z^1$ are as defined above, $Z^2$ is —NH— and Pr is the pyranyl- or t-butyl-dimethylsilyl (TBDMSi)-ether protecting group. This may be done by treating the amine with triphosgene and triethylamine in toluene at 60° C. to provide the corresponding isocyante, which is treated with a glutamate derivative of formula $R^9$—C(O)—CH(NH$_2$)—$Z^1$ where $R^9$ and Z are as defined above. Alternatively the corresponding glutamyl-isocyanate obtained from the corresponding glutamate by treatment with triphosgene and triethylamine in toluene at −78° C. may be reacted with the amine in a one pot procedure.

(ii) The compound of formula (VII) is deprotected to remove the TBDMSi or pyranyl groups by treatment with mild acidic media (AcOH, THF and H20 or PPTS, EtOH, 55° C.). This yields a compound of formula (VII) in which Pr is hydrogen. Compounds of the formula (V) in which Q is a leaving group may be prepared using standard reactions known in the art.

(iii) For example where Q is a succinimidyl group the compound of formula (VII) where Pr is hydrogen may be treated with disuccinimidyl-carbonate and triethylamine in acetonitrile. Where a 4-nitrophenyl carbonate group is desired treatment with 4-nitrophenyl chlorformate and triethylamine in THF may be used. A pentafluorophenyl carbonate may be added by in situ phosgenation of pentafluorophenol followed by coupling to the linker of formula (VII) in which Pr is hydrogen.

E: Compounds of the formula (V) in which $Z^2$ is —O—:

(i) The starting materials for the linkers possessing a carbamic bond are unsubstituted or substituted (with the group(s) $R^5_{(n)}$ (as defined above)) 4-hydroxy-benzylic alcohols. These type of linkers may require an extra electron withdrawing group on the aromatic nucleus in order to undergo 1,4-elimination. The 4-hydroxy group is specifically protected as an acetate by treating the starting material with acetyl-v-triazolo-[4,5-b]pyridine, 1 N NaOH in THF at 20° C. The alcohol function of the acetate is further protected as pyranyl- or TBDMSi-ether by the procedures described in section D above. The acetate function is then deprotected to restore the 4-hydroxy group in NaHCO3 aq. MeOH at 20° C. The resulting phenol compounds are reacted in a one pot procedure with a protected glutamyl-isocyanate as described in section D(i) above. This yields a compound of the formula of (VII) as shown above in which $Z^2$ is —O— and Pr is the pyanyl- or t-butyl-dimethylsilyl (TBDMSi)-ether protecting group.

(ii) Deprotection of this compound yields a compound of the formula (VII) in which Pr is hydrogen. This may be converted to compounds of the formula (V) by methods analogous to those described in sections D(ii) and (iii) above.

F: Alternative synthesis of compounds of formula (IV):

Compounds of the formula (IV) in which Q is hydrogen, fluoro, chloro, bromo or —O—(N-succinimide) may also be obtained by reference to WO95/02420 or WO95/03830.

E(ii). Other prodrugs.

Other compounds which may be used as prodrugs include p-nitro-benzyloxycarbonyl derivatives of cytotoxic compounds. Such compounds can be used in conjunction with a nitroreductase enzyme. It is believed that the nitroreductase enzyme converts the nitro group of the prodrug into a hydroxylamino or amino group, which results in the p-nitrobenzyloxycarbonyl moiety becoming activated and then self-immolating. This releases the active drug. These compounds include a compound of formula:

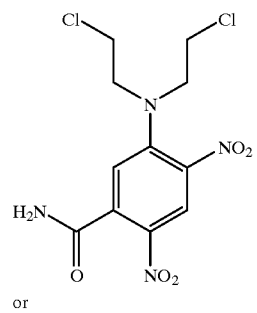

or

-continued

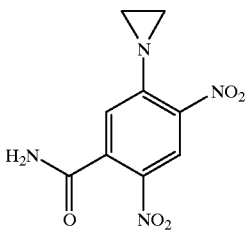

The nitroreductase enzyme of WO93/08288 requires a co-factor such as NADH or NADPH, and this may optionally be supplied as an additional component in the system of the invention.

Examples of other compounds described in the above references include prodrugs of actinomycin D, doxorubicin, daunomycin and mitomycin C. Prodrugs of the foregoing references are converted to active drugs by either nitroreductase or CPG2, although they may be modified to comprise protecting groups cleavable by other enzymes, eg β-lactamase or glucronidase.

Further prodrugs suitable for use in the invention include those of the general formula: FTLi-(PRT)$_{m'}$ or salts thereof where FTLi is a ras inhibitor such as a farnesyltransferase inhibitor compound and PRT represents m' protecting groups capable of being cleaved from the ras inhibitor by the action of an enzyme, where m' is an integer from 1 to 5. Such compounds are disclosed in WO95/03830.

Suitable FLTi's include those of the formula (VIII) or (IX)

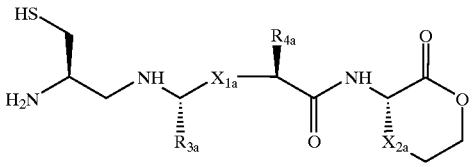

(VIII)

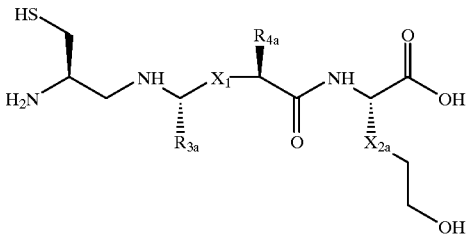

(IX)

where $R_{3a}$ and $R_{4a}$ are the side chains of naturally occurring amino acids (for example —CH$_3$, —CH(CH$_3$)$_2$, —CH$_2$CH(CH$_3$)$_2$, —CH(CH$_3$)CH$_2$CH$_3$, —CH$_2$OH, —CH$_2$CH$_2$SCH$_3$, —CH(OH)CH$_3$), including their oxidized forms (for example, methionine sulfoxide or methionine sulfone), or are substituted or unsubstituted aliphatic, aromatic or heteroaromatic groups, preferably cyclohexyl, phenyl, pyridyl, imidazolyl or saturated or unsaturated branched or straight chains of 2 to 8 carbon atoms optionally substituted with an aromatic or heteroaromatic ring;
$X_{1a}$ is CH$_2$CH$_2$, trans CH=CH or CH$_2$NH; and
$X_{2a}$ is (CH$_2$)$_n$ wherein n is 0, 1 or 2. Preferably $R_{3a}$ and $R_{4a}$ both represent CH(CH$_3$)CH$_2$CH$_3$.

Suitable FLTi compounds including those of formulae (VIII) and (IX) may be obtained by reference to WO95/03830.

Other suitable prodrugs for use in the system of the invention include those which are derivatized with a sugar or a β-lactam derivative. For example, suitable linkers which may be attached to active drugs of the type described above are:

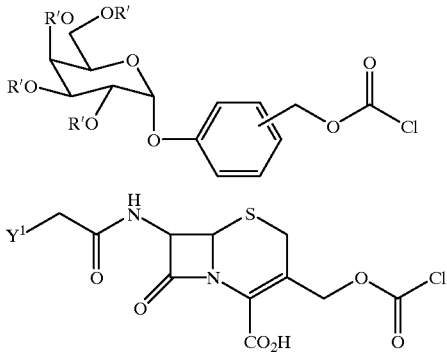

where R' is hydrogen or acetyl and Y' is aryl such as phenyl, benzyl or tolulyl, and these may be made in an analogous manner to the other prodrugs described above.

A further group of prodrugs are tyrphostin compounds of the general formula: PTKi-PRT$_{m'}$, where PTKi is a compound with PTK (protein tyrosine kinase) inhibitory activity, PRT is a protecting group capable of being cleaved from the PTK inhibitor by the action of an enzyme and m' is an integer from 1 to 5.

Suitable PTKs include tyrphostins. Tyrphostins are low molecular weight (e.g. less than 2,000) styryl containing inhibitors of protein tyrosine kinase which are capable of binding to the subsite of protein tyrosine kinase domains. Suitable tyrphostins include those described by Gazit et al (Gazit et al, J. Med. Chem. (1989) 32, 2344) and Gazit et al (J. Med. Chem. (1991) 43; 1896–1907) and especially tyrphostins of the general formula:

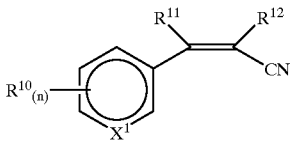

where $X^1$ represents carbon, a nitrogen or a group N→O; n is an integer from 1 to 3; each group $R_{10}$, which may be the same or different is hydrogen, hydroxy, mercapto, carboxy, formyl, $C_{1-4}$alkyl, $C_{2-4}$ alkenyl, $C_{1-4}$alkoxy, $C_{1-4}$alkylthio, carboxy$C_{1-4}$alkyl, carboxy$C_{2-4}$ alkenyl, $C_{1-4}$alkylsulphoxy, halo (ie. fluoro, chloro, bromo or iodo), nitro, amino, $C_{1-4}$alkylamino, or $C_{1-4}$dialkylamino, or when n is 2 or 3 two $R^{10}$ groups may together form a methylenedioxy or ethylenedioxy group; $R^{11}$ is hydrogen, hydroxy, $C_{1-4}$alkyl or together with position 2 of the ring to which the group(s) $R^{10}$ is(are) attached forms a 5 or 6 membered aliphatic or heterocyclic ring, said 5 or 6 membered ring optionally containing a ketone group; and $R^{12}$ is cyano, carboxy, carbamoyl, thiocarbamoyl, a group C(O)HNCH$_2$CN, a group C(NH$_2$)=C(CN)$_2$, an alpha keto group C(O)$R^{13}$ where $R^{13}$ is 3,4-dihydroxyphenyl or 2-thiophenyl or an alpha amido group C(O)NHR$^{14}$ where $R^{14}$ is benzyl, phenyl or 2,4-dimethoxyphenyl; provided that at least one of the groups $R^{10}$ and $R^{11}$ is mercapto, hydroxy or amino.

In a preferred embodiment, $X^1$ is C; n is an integer from 1 to 3; each group $R^{10}$, which may be the same or different is hydrogen, hydroxy, carboxy, formyl, $C_{1-4}$alkyl, $C_{2-4}$ alkenyl, $C_{1-4}$alkoxy, carboxy$C_{1-4}$alkyl, carboxy$C_{2-4}$ alkenyl, halo (ie. fluoro, chloro, bromo or iodo), nitro, amino, $C_{1-4}$alkylamino, or $C_{1-4}$dialkylamino, or when n is 2 or 3 two $R^{10}$ groups may together form a methylenedioxy or ethylenedioxy group; $R^{11}$ is hydrogen, hydroxy or $C_{1-4}$alkyl; and $R^{12}$ is cyano, carboxy, carbamoyl, thiocarbamoyl, a group C(O)HNCH$_2$CN or a group C(NH$_2$)=C(CN)$_2$. Most preferably, $X^{10}$ represents carbon, n is an integer from 1 to 3; each group $R^{10}$, which may be the same or different is hydrogen, hydroxy or amino; $R^{11}$ is hydrogen or hydroxy; and $R^{12}$ is cyano, a group C(O)HNCH$_2$CN, a group C(NH$_2$)=C(CN)$_2$, an alpha keto group C(O)$R^{13}$ where $R^{13}$ is 3,4-dihydroxyphenyl, or an alpha amido group C(O)NHR$^{14}$ where $R^{14}$ is benzyl; provided that at least one of the groups $R^{10}$, $R^{11}$, and $R^{12}$ are hydroxy or amino. Preferably, $R^{10}$ is hydroxy or amino. When $R^{11}$ forms a 5 or 6 membered ring with $R^{10}$ preferred rings include heterocyclic rings wherein the ring contain one nitrogen atom and 4 or 5 carbon atoms. The total number of atoms includes the 2 carbon atoms of the ring to which the group(s) $R^{10}$ is(are) attached.

Suitable tyrphostins such as the above may be obtained by the methods disclosed in, or analogous to those of, WO95/02420, Gazit et al 1989 and 1991, ibid, which are incorporated herein by reference.

Tyrphostins may be linked to any suitable protecting group which is removable by an enzyme. Suitable protecting groups PRT may be found by reference to WO95/03830 or WO95/02420 and may be of the structure:

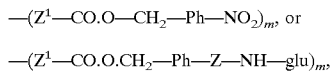

—(Z$^1$—CO.O—CH$_2$—Ph—NO$_2$)$_m$, or

—(Z$^1$—CO.O.CH$_2$—Ph—Z—NH—glu)$_m$, where $Z^1$ is as defined above or S, m' is an integer from 1 to 5, Ph is a phenylene ring optionally substituted by from 1 to 4 groups $R^5$ (which may be the same or different) as defined above and glu is a group —CHZ—C(O)—OR$^9$ where Z and $R^9$ are as defined above. The nitro group may be in the 2-position although is desirably in the 4-position of the ring relative to the Ph ring.

E(iii). Derivatives.

Physiologically acceptable derivatives of prodrugs include salts, amides, esters and salts of esters. Esters include carboxylic acid esters in which the non-carbonyl moiety of the ester grouping is selected from straight or branched chain $C_{1-6}$alkyl, (methyl, n-propyl,, n-butyl or t-butyl); or $C_{3-6}$cyclic alkyl (e.g. cyclohexyl). Salts include physiologically acceptable base salts, eg derived from an appropriate base, such as alkali metal (e.g. sodium), alkaline earth metal (e.g. magnesium) salts, ammonium and NR$_{4''}$ (wherein R" is $C_{1-4}$ alkyl) salts. Other salts include acid addition salts, including the hydrochloride and acetate salts. Amides include non-substituted and mono- and di-substituted derivatives.

F. Applications of the invention.

The system of the invention can be used in a method of treatment of the human or animal body. Such treatment includes a method of treating the growth of neoplastic cells which comprises administering to a patient in need of treatment the system of the invention. It is also possible that the invention may be used to treat cells which are diseased through infection of the human or animal body by bacteria, viruses or parasites. Viral late promoters often rely on viral proteins that are made early in the infection. The viral coat proteins which are expressed on the surface of an infected cell may be used as a target for getting the gene into the cell. If a viral late promoter is then used to direct expression of the GDEPT enzyme, any infected cells will express the protein, and specifically, cells which have been infected, for some time. This may be sufficient to kill the infected cells. For parasites, a parasite promoter and parasite surface proteins, may be used to direct expression and infect the parasites respectively.

For a bacteria, all the delivery systems will probably need to be changed to use bacterial viruses, although a specific promoter should be easier to define.

For use of the vectors in therapy, the vectors will usually be packaged into viral particles and the particles delivered to the site of the tumour, as described in for example Ram et al (ibid). The viral particles may be modified to include an antibody, fragment thereof (including a single chain) or tumour—directed ligand to enhance targetting of the tumour. Alternatively the vectors may be packaged into liposomes. The liposomes may be targeted to a particular tumour. This can be achieved by attaching a tumour-directed antibody to the liposome. Viral particles may also be incorporated into liposomes. The particles may be delivered to the tumour by any suitable means at the disposal of the physician. Preferably, the viral particles will be capable of selectively infecting the tumour cells. By "selectively infecting" it is meant that the viral particles will primarily infect tumour cells and that the proportion of non-tumour cells infected is such that the damage to non-tumour cells by administration of a prodrug will be acceptably low, given the nature of the disease being treated. Ultimately, this will be determined by the physician.

One suitable route of administration is by injection of the particles in a sterile solution. While it is possible for the prodrugs to be administered alone it is preferable to present them as pharmaceutical formulations. The formulations comprise a prodrug, together with one or more acceptable carriers thereof and optionally other therapeutic ingredients. The carrier or carriers must be "acceptable" in the sense of being compatible with the other ingredients of the formulation and not deleterious to the recipients thereof, for example, liposomes. Suitable liposomes include, for example, those comprising the positively charged lipid (N[1-(2,3-dioleyloxy)propyl]-N,N,N-triethylammonium (DOTMA), those comprising dioleoylphosphatidylethanolamine (DOPE), and those comprising 3β[N-(n',N'-dimethylaminoethane)-carbamoyl]cholesterol (DC-Chol).

Viruses, for example isolated from packaging cell lines may also be administered by regional perfusion or direct intratumoral direction, or direct injection into a body cavity (intracaviterial administration), for example by intraperitoneum injection.

It is also known that muscle cells can take up naked DNA and thus sarcomas may be treated using a vector system of the invention in which naked DNA is directly injected into the sarcoma.

Formulations suitable for parenteral or intramuscular administration include aqueous and non-aqueous sterile injection solutions which may contain anti-oxidants, buffers, bacteriostats, bactericidal antibiotics and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. The formulations may be presented in unit-dose or multi-dose containers, for example sealed ampoules and vials, and may be stored in a freeze-dried (lyophilized) condition requiring only the addition of the sterile liquid carrier, for example water, for injections, immediately prior to use. Injection solutions and suspensions may be prepared extemporaneously from sterile powders, granules and tablets of the kind previously described.

It should be understood that in addition to the ingredients particularly mentioned above the formulations may include other agents conventional in the art having regard to the type of formulation in question. Of the possible formulations, sterile pyrogen-free aqueous and non-aqueous solutions are preferred.

The doses may be administered sequentially, eg. at daily, weekly or monthly intervals, or in response to a specific need of the patient. Preferred routes of administration are oral delivery and injection, typically parenteral or intramuscular injection or intratumoural injection.

In using the system of the present invention the prodrug will usually be administered following administration of the vector encoding an enzyme. Typically, the vector will be administered to the patient and then the uptake of the vector by transfected or infected (in the case of viral vectors) cells monitored, for example by recovery and analysis of a biopsy sample of targeted tissue.

The exact dosage regime will, of course, need to be determined by individual clinicians for individual patients and this, in turn, will be controlled by the exact nature of the prodrug and the cytotoxic agent to be released from the prodrug but some general guidance can be given. Chemotherapy of this type will normally involve parenteral administration of both the prodrug and modified virus and administration by the intravenous route is frequently found to be the most practical. For glioblastoma the route is often intratumoural. A typical dosage range of prodrug generally will be in the range of from about 1 to 150 mg per kg per patient per day, which may be administered in single or multiple doses. Preferably the dose range will be in the range from about 10 to 75, e.g. from about 10 to 40, mg per kg per patient per day. Other doses may be used according to the condition of the patient and other factors at the discretion of the physician.

Tumours which may be treated using the system of the present invention include any tumours capable or being treated by a GDEPT or VDEPT system and thus are not limited to any one particular class of tumours. Particularly suitable tumour types include breast, colorectal and ovarian tumours, as well as pancreatic, melanoma, glioblastoma, hepatoma, small cell lung, non-small cell lung, muscle and prostate tumours.

The system of the invention may also be used to treat infections diseases, for example, and any other condition which requires eradication of a population of cells.

It will be understood that where treatment of tumours is concerned, treatment includes any measure taken by the physician to alleviate the effect of the tumour on a patient. Thus, although complete remission of the tumour is a desirable goal, effective treatment will also include any measures capable of achieving partial remission of the tumour as well as a slowing down in the rate of growth of a tumour including metastases. Such measures can be effective in prolonging and/or enhancing the quality of life and relieving the symptons of the disease.

The following Examples illustrate the invention.

PREPARATIVE EXAMPLE 1

In order to express CPG2 on the surface of mammalian cells, a fusion between CPG2 and portions of c-erbB2 were constructed. The portions of c-erbB2 used are:

1. The signal peptide encoding region (codons 1–27 SEQ ID NO: 2): 5'>ATG GAG CTG GCG GCC TTG TCC CGC TGG GGG CTC CTC CTC GCC CTC TTG CCC CCC GGA GCC GCG AGC ACC CAA GTG TGC ACC<3'

This is identical to the sequence published by Coussens et al (1985) Science 230, 1132–1139, apart from a silent, natural CGC to CGT mutation that occurs in codon 8, but does not alter the amino acid at this position.

2. The transmembrane region (codons 636–686 SEQ ID NO: 3): 5'>GAC CTG GAT GAC AAG GGC TGC CCC GCC GAG CAG AGA GCC AGC CCT CTG ACG TCC ATC GTC TCT GCG GTG GTT GGC ATT CTC CTG GTC GTG GTC TTG GGG GTG GTC TTT GGG ATC CTC ATC AAG CGA CGG CAG CAG AAG ATC CGG AAG TAC ACG<3'

This is identical to the sequence published by Coussens et al (1985) Science 230, 1132–1139, apart from a natural mutation in codon 655, which causes a conserved Val (GTC) to Ile (ATC) substitution.

In order to facilitate joining of the signal peptide of c-erbB2 to CPG2, a PCR fragment was generated which contained codons 1–27 of c-erbB2, with codons 28 and 29 mutated to convert them to a BamH1 (GGATCC) restriction endonuclease site. This was achieved using primer #4478 (SEQ ID NO: 4):

5'>GCT TAC AAT TGC TTC TGA CAC<3' in conjunction with primer #4479 (SEQ ID NO: 5):

5'>CGC GGA TCC GGT GCA CAC TTG GGT GCT C<3'

The signal peptide containing fragment was released from the PCR fragment by digestion with BamH1 and Nco1 (a site occurs in c-erbB2 which straddles the initiator ATG—i.e CCATGG).

By a similar approach, codons 21 and 22 of CPG2 were converted into a BamH1 site. At the same time, an EcoR1 site was created at codon 416 (the natural stop codon) of CPG2. This was done using the PCR primer #4476(SEQ ID NO: 6):

5'>CGC GGA TCC GCC CTG GCC CAG AAG CGC<3' in conjunction with primer #4477 (SEQ ID NO: 7):
5'>CGC GAA TTC CTT GCC GGC GCC CAG ATC<3'

Similarly, codons 634 and 635 of c-erbB2 were converted to an EcoR1 site and codons 687 and 688 to a Cla1 site. This was achieved using the primer #4480(SEQ ID NO: 8):
5'>CGC GAA TTC GAC CTG GAT GAC AAG GGC<3' in conjunction with primer #4481 (SEQ ID NO: 9):
5'>CGC ATC GAT CGT GTA CTT CCG GAT CCT<3'.

The transmembrane region of c-erbB2 (codons 636–686) was released as a PCR fragment digested with EcoR1 and Cla1.

Finally, two oligonucleotide adaptors were used to generate a 9E10 monoclonal antibody recognition site (see Evan et al (1985) Mol Cell Biol 5, 3610–3616.) to the 5' end of the c-erbB2 transmembrane region . This was achieved by using oligonucleotide #4513: 5'>CGA TGA GCA GAA GCT GAT ATC CGA GGA GGA CCT GAA<3' and oligonucleotide #4514 (SEQ ID NO: 11):
5'>CTA GTT CAG GTC CTC CTC GGA TAT CAG CTT CTG CTC AT<3' together with standard linker cloning techniques. The various fragments were joined to each other through the engineered restriction endonuclease sites to generate a chaemera that produces a protein with the structure:

c-erbB2 (amino acids 1–27): GlySer: CPG2 (amino acids 23–415): GluPhe: c-erbB2 (amino acids 636–686): IleAsp: 9E10 epitope (GluGlnLysLeuIleSerGluGluAspLeu): Asn*.

The extra amino acids between each portion of the fusion are a consequence of the engineered restriction enzyme sites. This fusion gene is referred to as "CPG2 (surface)". A variation of this gene was created in which a frame shift mutation was introduced between the c-erbB2 signal peptide and the CPG2 portion. This was achieved by digesting the chaemera with BamH1, end repairing the overhangs and re-ligating the plasmid. This produces an out of frame mutation, which results in a gene that cannot express CPG2 (surface) and is referred to as "CPG2(surfaceF/S)". CPG2 (surface) and CPG2(surfaceF/S) were cloned into the mammalian expression vector MLVβplink, which uses a moloney murine leukaemia virus LTR to direct expression of genes in murine cell lines (Dalton and Treisman, (1992), Cell 68, 597–612). These plasmids are referred to as MLVCPG2 (surface) and MLVCPG2(surfaceF/S) respectively.

COMPARATIVE EXAMPLE 1

In order to assess the expression of CPG2(surface) in mammalian cells, one dish of NIH3T3 cells was transfected with MLVCPG2(surface) and as a negative control, one dish of cells with MLVβplink. The transfections were performed with the lipid transfection reagent lipofectAMINE (GibcoBRL). For transfection, $1 \times 10^5$ cells were plated into 35 mm tissue culture dishes and incubated at 37° C. overnight. The following day, lipofectAMINE:DNA complexes were prepared by combining 0.4 μg of plasmid with 6 μl of lipofectAMINE reagent in a total of 32 μl of PBSA; the complexes were incubated at room temperature for 15 minutes. The cells were washed twice with 2 ml of serum free DMEM medium and placed in 0.8 ml of serum free DMEM. The lipofectAMINE:DNA complexes were diluted into 0.2 ml of serum free medium and added to the cells. The cells were incubated with the lipofectAMINE:DNA complexes for 6 hours at 37° C., washed twice with 2 ml of DMEM medium containing 10% foetal calf serum (FCS) and placed into. 2.5 ml 10% FCS/DMEM. After a further incubation period of 42 hours, the cells were washed twice with 5 ml PBSA and extracted on the tissue culture dishes into 50 μl of buffer A (250 mM Tris.HCl, 10% v/v glycerol, 1% v/v Triton X-100, pH7.5). The extract was transferred into 1.5 ml tubes, centrifuged at 13,000 rpm in a micro-fuge. The supernatants were collected and the protein concentration was determined with the Bio-Rad protein assay kit, with BSA as a standard.

For protein-immunoblot analysis, 10 μl of each extract was combined with 10 μl of SDS sample buffer and the proteins were separated on a 10% SDS-polyacrylamide gel (Laemmli U.K. (1970) Nature 227; 680–685). The proteins in the gel were transferred to nitrocellulose by electroelution and the cell extracts analysed by protein immuno-blotting (Gershoni J. M. and Palade G. E. (1983) Anal. Biochemistry 131;1–15), using a CPG2 specific rabbit polyclonal antibody which was raised to CPG2 expressed in Sf9 insect cells. The antibody was used at a dilution of 1:1000 and the immuno-complexes detected using the ECL immunoblotting kit, according to the manufacturers instructions (Amersham).

These results show that in the extracts from the cells transfected with pMLVCPG2 (surface) there is a protein recognised by the antibody that runs as a smear with a Mr of ~50,000–60,000 (FIG. 1, lane 2). This protein is not present in cells transfected with MLVβplink (lane 1) and therefore demonstrates that CPG2(surface) is expressed at high levels in these cells.

The extracts were tested for CPG2 enzyme activity by measuring their ability to cleave the CMDA prodrug into drug (springer et al Eur J Cancer (1991) 27; 1361–1366), which can be detected by measuring light absorbance at 305 nm. For the assay, 5 μg of NIH3T3 protein extracted in buffer A was incubated in 1 ml of assay buffer (2 mM Tris.HCl, 1 mM MgCl2, 60 μM ZnCl2, pH 7.4) containing 50 μM CMDA prodrug, at 37° C. for 15 min. After incubation, EDTA was added to a final concentration of 10 mM and the resulting change in absorbance at 305 nm was compared to that of the starting solution. A reduction in absorbance indicates conversion of the prodrug into drug and therefore by inference demonstrates the presence of CPG2. Under these conditions, no CPG2 activity could be detected in extracts from cells transfected with either MLVβplink or MLVCPG2 (surface) indicating that the expressed protein was inactive.

COMPARATIVE EXAMPLE 2

Since CPG2(surface) is likely to be processed through the Golgi apparatus and endoplasmic reticulum to reach the surface of the cells (the route taken by c-erbB2) it was considered that it could potentially be glycosylated and that this may account for the lack of enzyme activity. N-linked glycosylation occurs in the golgi apparatus and endoplasmic reticulum at a motif whose primary amino acid sequence is Asn-Xaa-Ser/Thr (where Xaa is any amino acid); the glycosylation occurs on the Asn residue. Within the primary amino acid sequence of CPG2, there are three such consensus motifs, located at residues Asn222, Asn 264 and Asn 272. To establish whether CPG2(surface) was glycosylated, two sets of transfected cells were set up. Each set contained a dish of cells transfected with MLVCPG2(surface), and a dish transfected with MLVCPG2(surface/FS) as a negative control. Following the transfection, set 1 was incubated in 10% FCS/ DMEM for 42 hours. Set 2 was also incubated in 10% FCS/ DMEM for 42 hours, but tunicamycin (0.1 mg/ml final concentration), was included in the medium for the last 24 hours of the incubation. Tunicamycin is a nucleoside antibiotic that inhibits N-linked glycosylation. The cells were harvested into buffer A and subjected to protein immunoblot analysis and to CPG2 enzyme activity assay as described above.

Figure 2A:
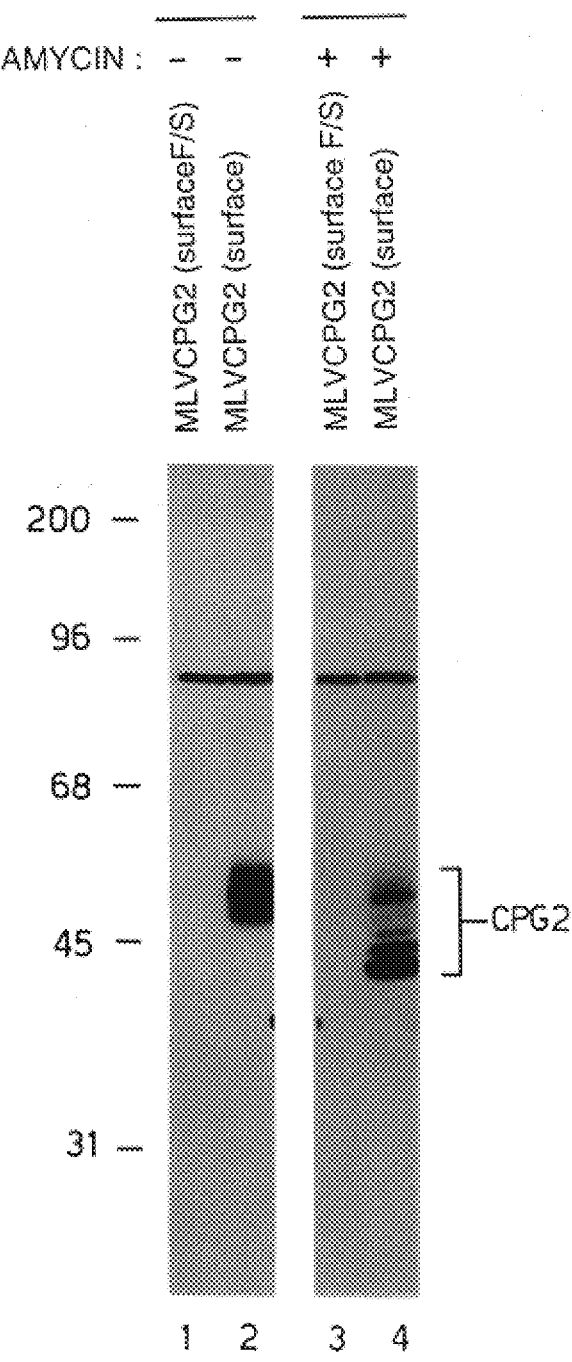
FIG. 2A shows (A) Immunoblot analysis. NIH3T3 cells were transfected with either MLVCPG2(surfaceF/S) (lanes 1, 3) or MLVCPG2(surface) (lanes 2, 4). The cells were incubated in the absence of tunicamycin (lanes 1, 2) or in the presence of tunicamycin (lanes 3, 4). Extracts were prepared and analysed as described in FIG. 1. The position of migration of CPG2 (surface) is indicated, as is the position of migration of standard molecular weight markers (in kDa), to the left of the figure.

The immunoblot data show that when CPG2(surface) is produced in mammalian cells that are incubated in the presence of tunicamycin, its mobility in SDS-polyacrylamide gels increases compared to cells incubated in the absence of tunicamycin (FIG. 2, compare lanes 2 and 4). Furthermore, the protein undergoes a 'laddering', suggestive of a block occuring in glycosylation. Some of the protein does appear to escape the block, but it is likely that this represents proteins that were synthesised before the tunicamycin was applied. The control lanes show that CPG2 (surface) is not produced in cells transfected with MLVCPG2(surfaceF/S) (FIG. 2, lanes 1,3).

Figure 2B:
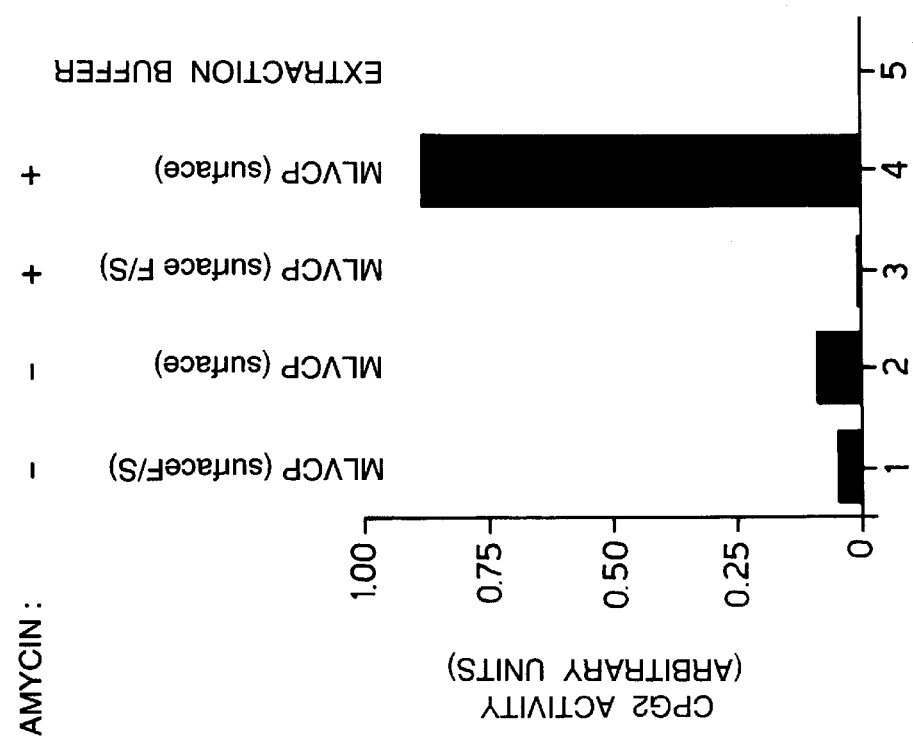
FIG. 2B shows (B) CPG2 enzyme activity assay. The enzyme extracts from the cells in part (A) were analysed for CPG2 enzyme activity. Sample numbers correspond to lane numbers for part (A); sample 5 contains extraction buffer instead of cell extract as a negative control. The activity is expressed as arbitrary values relative to buffer controls.

These protein extracts were analysed for CPG2 enzyme activity as described above. Extracts from cells transfected with MLVCPG2(surface/FS) did not contain any significant enzymatic activity in cells that were treated or untreated with tunicamycin (FIG. 2B, samples 1,3). Extracts from cells transfected with MLVCPG2(surface) and not treated with tunicamycin also did not contain any CPG2 activity (FIG. 2B, sample 2). However extract from cells transfected with MLVCPG2(surface) and treated with tunicamycin contained high level of CPG2 activity that could be detected in this assay (FIG. 2B, sample 4).

These data show that CPG2(surface) expressed in NIH3T3 cells is glycosylated and that this glycosylation inhibits its enzymatic activity. However, when glycosylation is blocked, then the enzyme is active.

Example 1

In order to prevent glycosylation of CPG2(surface), a series of mutant genes were constructed containing specific codon substitutions that were designed to disrupt the glycosylation motifs. In the first series, individual mutations were created that converted amino acids Asn222, Asn264 or Asn272 to leucine residues. These were generated by PCR, using the primers set out below.

1) For Asn222. Primer #538 (SEQ ID NO: 12): 5'>CCG GCA TGC GAG GCC TTG CCG GTG ATG AGG ACC TGC AC<3'

This was used in conjunction with primer #4732 (SEQ ID NO: 13): 5'>CGA AGG CCC CGT TCC GCG<3'

2) For Asn264. Primer #539 (SEQ ID NO: 14): 5'>CTG CGC TTC CTC TGG ACC ATC<3'

Primer #540 (SEQ ID NO: 15): 5'>GAT GGT CCA GAG GAA GCG CAG<3'

These were used in conjunction with primer #4733 (SEQ ID NO: 16); 5'>TGC AGG TCA ACA TCA CCG<3' and primer #557 (SEQ ID NO: 17): 5'>TTC TTG CCG CCT TCG CCG GC<3'

3) For Asn272. Primer #541 (SEQ ID NO: 18): 5'>AAG GCC GGC CTC GTC TCG AAC<3'

Primer #542 (SEQ ID NO: 19): 5'>GTT CGA GAC GAG GCC GGC CTT<3'

These were used in conjunction with primers #4733 and 557.

For Asn222, a PCR fragment was produced containing the mutated residue on a Sma1/Sph1 fragment which was used to replace the wild type sequences. For residues Asn264 and Asn 272, the relevent PCR fragments were generated as Sph1/Not1 fragments and these was used to replace the wild type sequences in the CPG2 gene. All three mutants were cloned into the context of MLVCPG2(surface) and are referred to as MLVCPG2(surface)LNN for the mutant Asn222Leu; MLVCPG2(surface)NLN for the mutant Asn264Leu and MLVCPG2(surface)NNL for the mutant Asn272Leu.

In order to test if the potential sites were glycosylated, two sets of NIH3T3 cells were prepared. Each set contained one dish of cells transfected with MLVCPG2(surface), one dish of cells transfected with MLVCPG2 (surface) LNN, one dish of cells transfected with MLVCPG2(surface)NLN, and one dish of cells transfected with MLVCPG2(surface)NNL. Set 1 were incubated in the absence of tunicamycin and Set 2 in the presence of tunicamycin as described above. Cell extracts were prepared in buffer A and protein immunoblot analysis and CPG2 enzymatic activity assays performed.

Figure 3A:
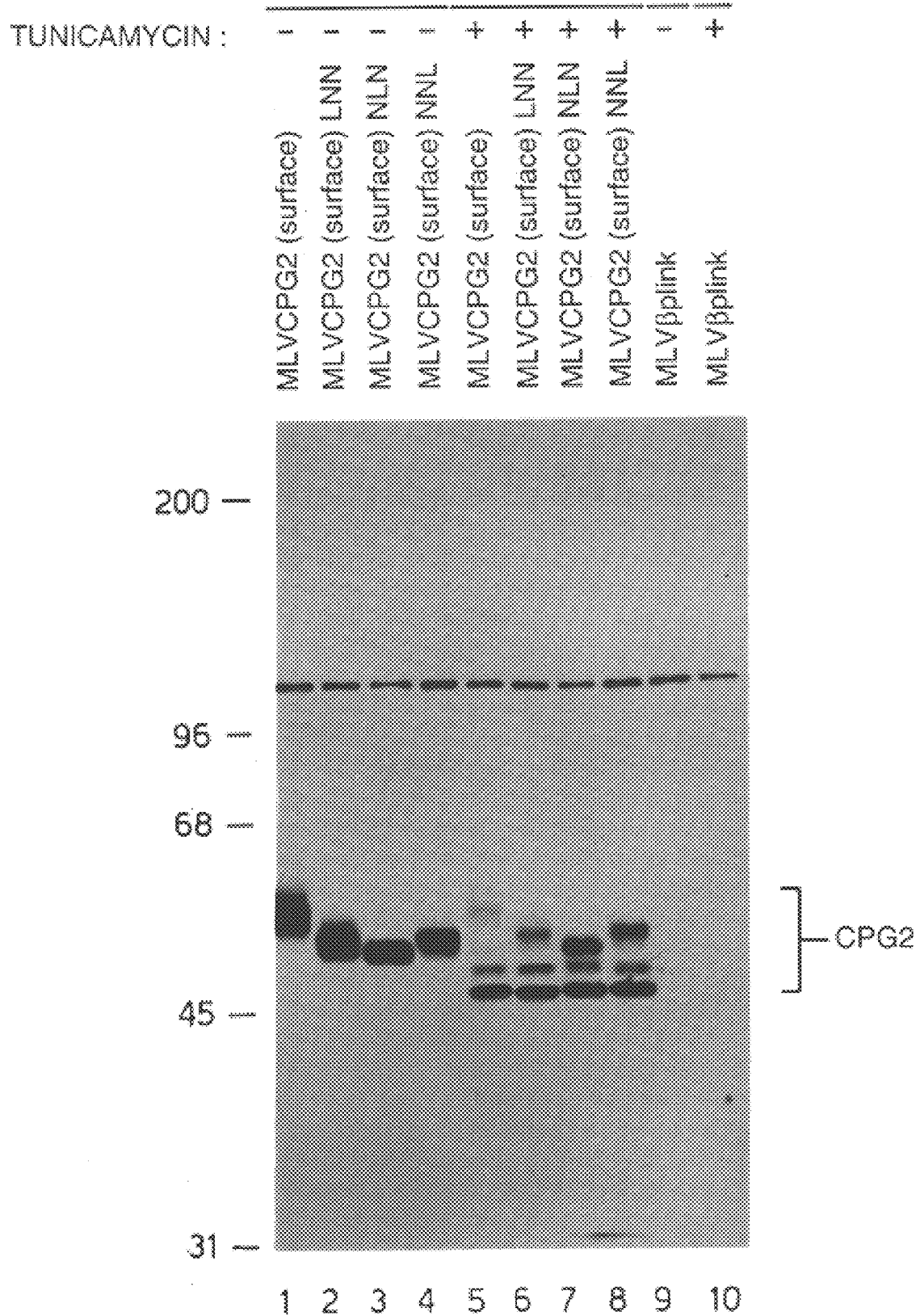
FIG. 3A shows (A) immunoblot analysis. NIH3T3 cells were transfected with MLVCPG2 (surface) (lanes 1, 5); MLVCPG2 (surface)LNN (lanes 2, 6); MLVCPG2 (surface) NLN (lanes 3, 7); MLVCPG2 (surface) NNL (lanes 4, 8) or MLVβplink (lanes 9, 10). Samples come from either control cells (lanes 1, 2, 3, 4, 9) or from cells treated with tunicamycin (lanes 5, 6, 7, 8, 10). The samples were analysed as in FIG. 1. The position of migration of the various forms of CPG2(surface) is indicated, as is the position of migration of the standard molecular mass markers (in kDa), to the left of the figure.

The immunoblot data shows that each of the individual mutations results in an increase in mobility of CPG2 (surface) in SDS-polyacrylamide gels (FIG. 3A, lanes 1–4). In the presence of tunicamycin, the mobility of the mutant non-glycosylated proteins is identical to that of CPG2 (surface) (FIG. 3A, lanes 5–8). These data indicate that the increased mobility seen in the absence of tunicamycin is not due to the effect of the mutations on the mobility of CPG2(surface) in SDS-polyacrylamide gels and indicate that each of the three potential sites is glycosylated in NIH3T3 cells.

Figure 3B:
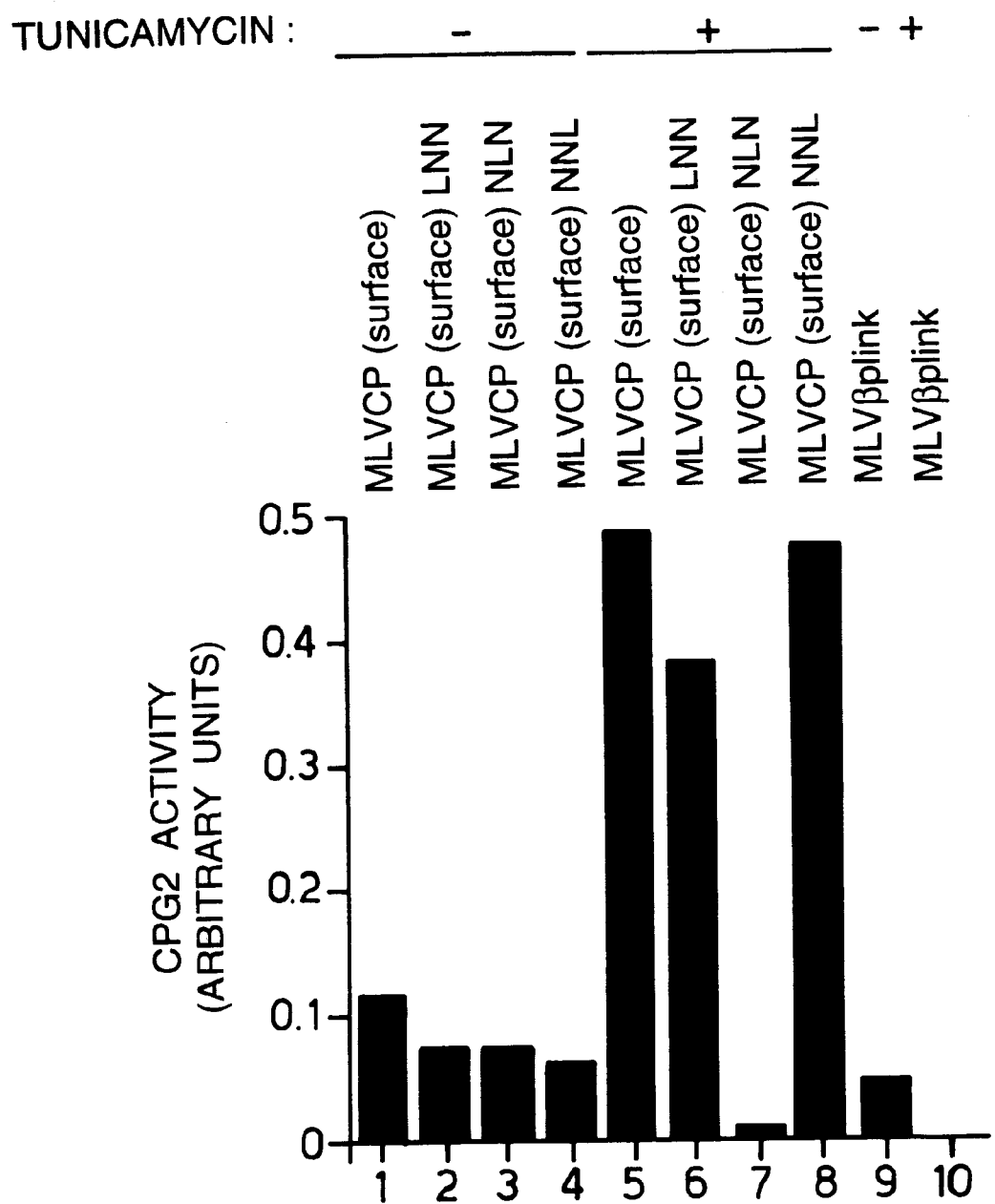
FIG. 3B shows (B) CPG2 enzyme activity assay. The cell extracts from part (A) were analysed by CPG2 enzyme activity assay. Sample numbers correspond to lane numbers from part (A). The activity is expressed as arbitrary values, relative to buffer controls.

The extracts were subjected to CPG2 enzyme activity assay as described above. All three mutant proteins were found to be inactive when produced in NIH3T3 cells not treated with tunicamycin as is seen with the unmutated protein (FIG. 3B, samples 1–4). However, when produced in tunicamycin treated NIH3T3 cells, CPG2 (surface), CPG2 (surface) LNN and CPG2 (surface) NNL were all found to be active, whereas CPG2 (surface) NLN was found to be inactive (FIG. 3B, samples 5–8).

Taken together, these data indicate that each of the identified potential glycosylation motifs is glycosylated in NIH3T3 cells and that mutations that disrupt the motifs prevent glycosylation. Individual mutation of residues Asn222 and Asn272 has no effect on enzyme activity, but mutation of Asn264 blocks enzymatic activity.

A variation of the mutation at the glycosylation motif at Asn 264 was therefore produced. It is possible to block glycosylation by mutation of the Ser/Thr at the third position in the motif. Therefore, Thr266 was mutated to a Leucine using primer #766 (SEQ ID NO: 20): 5'>TCC AAC TGG GTC ATC GCC AAG<3' and primer #767 (SEQ ID NO: 21): 5'>CTT GGC GAT GAC CCA GTT GAA<3' in conjunction with primers #4733 and #577 and following the same strategy as for mutations at residues 264 and 272. Mutation Thr266Leu was cloned into the context of mutations Asn222Leu and Asn272Leu to produce a triple mutated gene referred to as CPG2(surface)LNLL. This was cloned into MLVβplink and is referred to as MLVCPG2 (surface)LNLL.

Figure 4A:
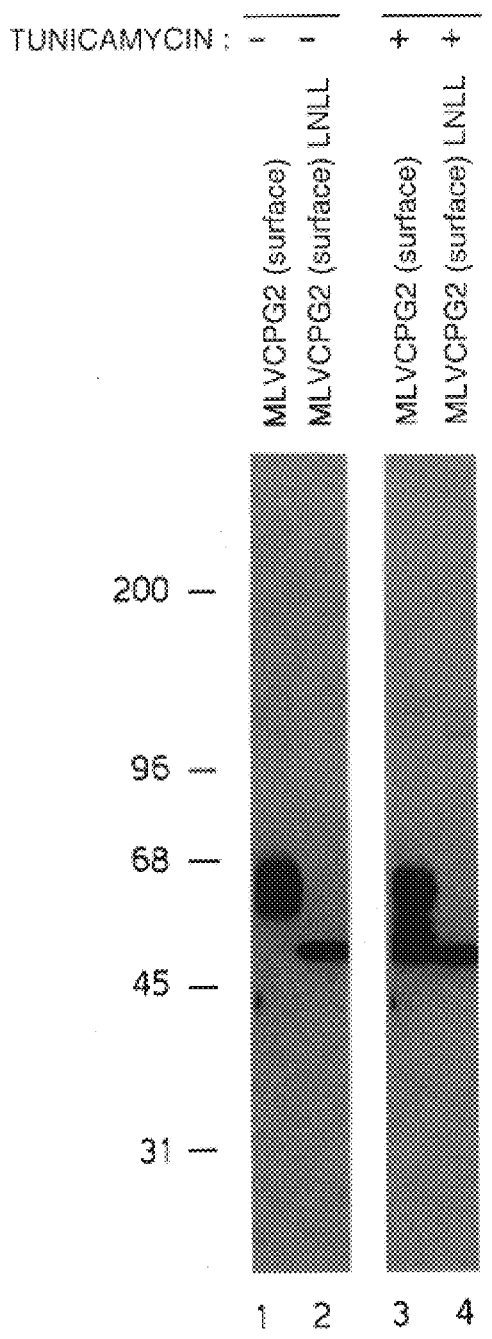
FIG. 4A shows (A) immunoprotein blot analysis. NIH3T3 cells were transfected with MLVCPG2 (surface) (lanes 1, 3) or with MLVCPG2 (surface)LNLL (lanes 2, 4). The extracts are from control cells (lanes 1, 2) or from cells treated with tunicamycin (lanes 3, 4). The samples were analysed as for FIG. 1. The position of migration of the CPG2 (surface) proteins is indicated, as is the position of migration of standard molecular mass markers (in kDa), to the left of the lanes.
Figure 4B:
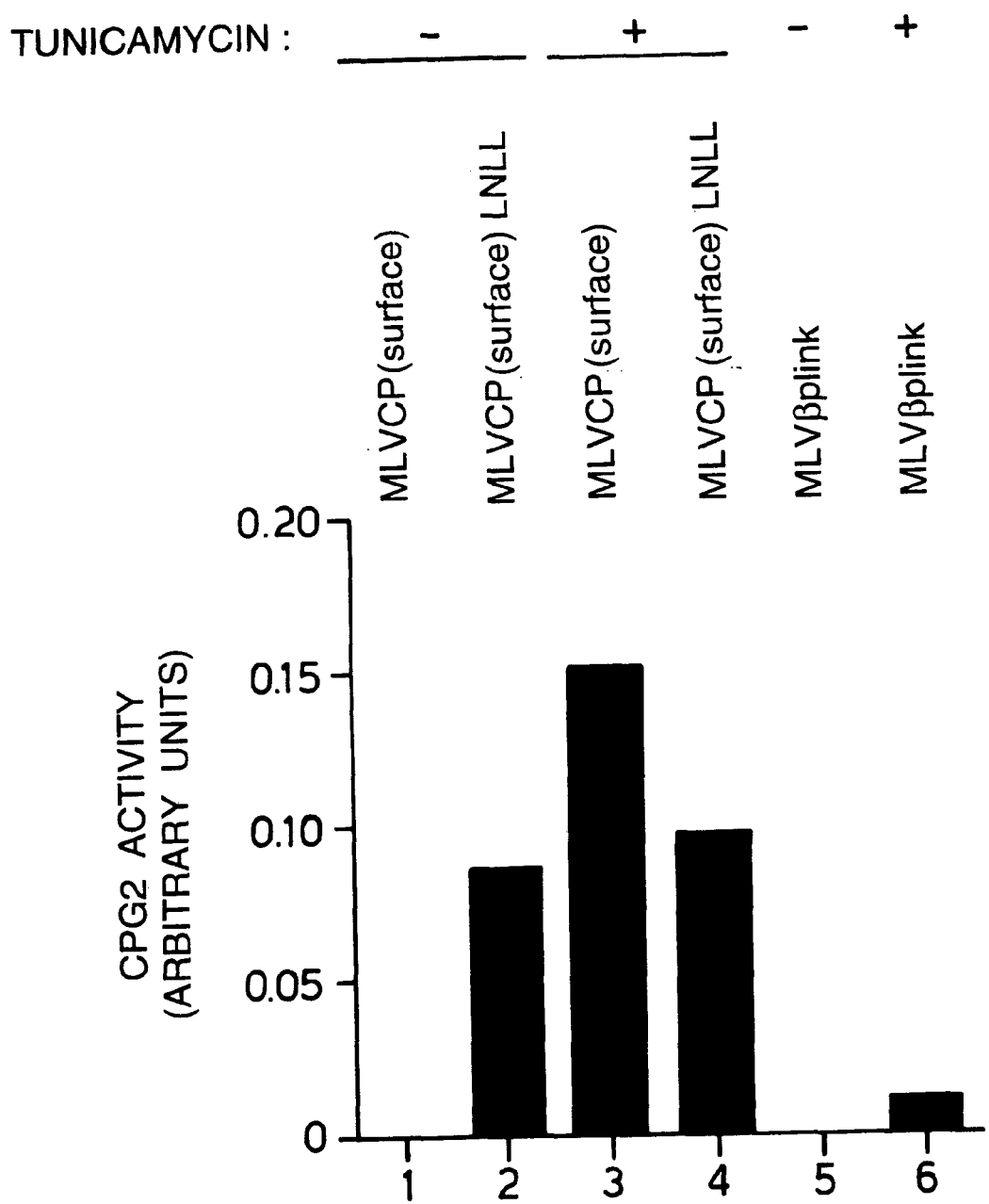
FIG. 4B shows (B) CPG2 enzyme activity assay. The cell extracts from part (A) were analysed by CPG2 enzyme activity assay. Sample numbers correspond to lane numbers from part (A); additionally, samples from cells transfected with MLVβplink (samples 5, 6) either from control cells (Sample 5) or from cells treated with tunicamycin (sample 6) are included as negative controls. The results are expressed in arbitrary values relative to buffer controls.

To test if this protein is glycosylated and if it was active, two sets of NIH3T3 cells were prepared, each of which contained one dish of cells transfected with MLVCPG2 (surface) and one dish of cells transfected with MLVCPG2 (surface)LNLL. Set 1 was incubated in the absence of tunicamycin and set 2 in the presence of tunicamycin as described. Cell extracts were prepared in buffer A and subjected to protein immunoblot analysis and enzyme activity assay. The immunoblot analysis shows that CPG2 (surface)LNLL migrates as a tight band on SDS-polyacrylamide gels with an apparent Mr of ~47,000; this is considerably smaller than that of CPG2(surface) (FIG. 4A, lanes 1,2). When CPG2(surface)LNLL is produced in cells incubated with tunicamycin, there is no change in its apparent molecular mass (lanes 2,4). Furthermore, CPG2(surface) LNLL co-migrates with the fastest migrating (and therefore presumably non-glycosylated) form of CPG2(surface) produced in NIH3T3 cells treated with tunicamycin (FIG. 4B, lanes 2,3).

The enzymatic activity of these extracts was examined. Unlike the CPG2(surface), CPG2 (surface) LNLL was found to be active in extracts taken from cells that had not been treated with tunicamycin (FIG. 4B, samples 1,2). CPG2 from cells that had been treated with tunicamycin did not affect this activity, in contrast to CPG2(surface) from tunicamycin treated cells (compare samples 1,3 with 2,4).

These data indicate that mutations of all three glycosylation motifs in CPG2(surface) inhibit completely its glycosylation in NIH3T3 cells. Mutation Asn222Leu blocked glycosylation of that residue and was permissive for enzyme activity. Mutation Asn264Leu blocked glycosylation of that residue but also inhibited enzyme activity. Mutation Thr266Leu blocked glycosylation on residue Asn264, and was permissive for activity. Mutation Asn272Leu blocked glycosylation at that residue and was permissive for activity. The triple mutant Asn222Leu, Thr266Leu, Asn272Leu was not glycosylated and was active.

Example 2

The ability of CPG2(surface) to kill NIH3T3 cells in the presence of the CMDA pro-drug was examined. Three sets of NIH3T3 cells were prepared, each of which contained one dish of cells transfected with MLVβplink, one dish of cells transfected with MLVCPG2(surface) or one dish of cells transfected with MLVCPG2(surface)LNLL. The cells were incubated for 42 hours following the transfection and then set 1 was incubated in the presence of prodrug vehicle (5 mM Hepes, 0.5% v/v DMSO, pH7.0; final concentrations) for 24 hours. Set 2 was incubated in the presence of the CMDA prodrug (0.5 mM final concentration) for 3 hours. Set 3 was incubated in CMDA (0.5 mM) for 24 hours. Following prodrug treatment, the cells were washed three times with 5 ml 10% FCS/ DMEM and sets 1 and 3 incubated in fresh medium for a further 24 hours, set 2 for 45 hours. The cells were then passaged into fresh culture dishes, seeded at $1\times10^5$ cells/ 35 mm dish in 2 ml FCS/ DMEM. After a further 72 hour incubation cell growth was assessed by [3H]-thymidine incorporation.

For thymidine incorporaion, 1 $\mu$Ci of [methyl-$^3$H] thymidine was added to each well (2 ml medium) and incubated for 5 hours at 37° C. The cells were washed twice with PBSA (4° C.) and fixed with 5% w/v trichloroacetic acid (TCA) in water at 4° C. for 20 minutes. The TCA was removed and the cells washed twice with 2 ml methanol and air dried. The DNA was extracted with 1 ml 0.1 M NaOH, 1% SDS at room temperature for 5 minutes, added to 4 ml scintilation fluid and the incorporated thymidine determined by scintillation counting.

Figure 5:
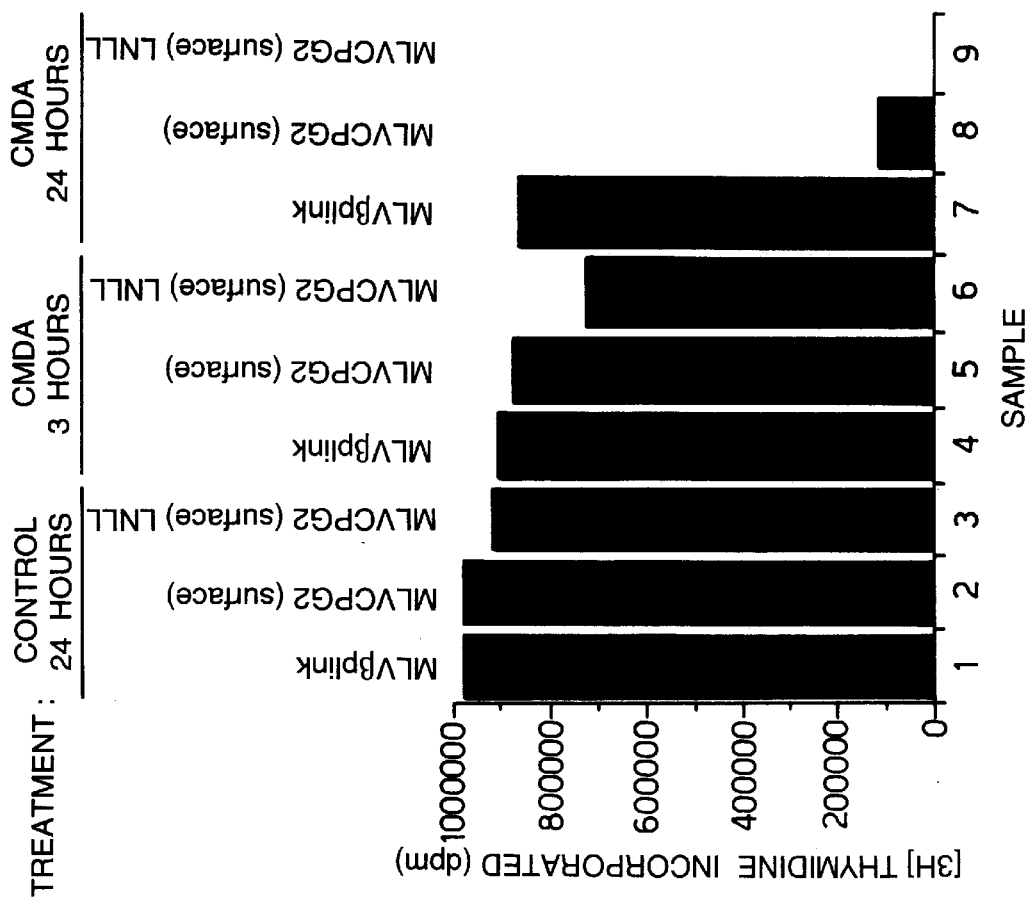
FIG. 5. cytotoxicity assay NIH3T3 cells were transfected with MLVβplink (samples 1, 4, 7) MLVCPG2 (surface) (lanes 2, 5, 8) or MLVCPG2(surface)LNLL (lanes 3, 6, 9). Forty two hours after transfection, the cells were treated with prodrug vehicle for 24 hours as a control (lanes 1–3), with CMDA prodrug for 3 hours (lanes 4–6) or with CMDA prodrug for 24 hours (lanes 7–9). After a recovery period, the cells were passaged into fresh tissue culture dishes and after 3 days, the viability of the cells determined by measuring [methyl-$^3$H]thymidine incorporation. The amount of incorporated thymidine is shown in terms of dpm for each sample.

Cells that had been transfected with either MLVCPG2 (surface) or MLVCPG2(surface)LNLL grew at the same rate as cells transfected with MLVβplink, indicating that expression of CPG2(surface) or CPG2 (surface) LNLL on the surface of mammalian cells does not affect cell growth rates (FIG. 5, samples 1–3). Prodrug treatment of the control cells had minimal effect on their growth rate (FIG. 5, samples 1, 4, 7). By contrast, prodrug treatment of the cells expressing CPG2(surface) and CPG2(surface)LNLL had a marked effect on their growth. Cells expressing CPG2(surface) were unaffected by a 3 hour prodrug treatment, but there was an –87% inhibition of cell growth following a 24 hour prodrug treatment (FIG. 5, samples 2, 5, 8). Cells expressing CPG2 (surface)LNLL were even more sensitive to prodrug treatment, showing a –20% reduction in cell growth following a 3 hour prodrug treatment and complete cell death following a 24 hour prodrug treatment.

These data show that when NIH3T3 cells expressing CPG2 (surface) are treated with the CMDA prodrug, cells growth can be prevented. Blocking glycosylation of CPG2 (surface) increased the enzyme activity and resulted in greatly increased cell kill potential of the enzyme-prodrug system.

Preparative Example 2

1. Construction of the vector

An expression cassette was constructed by fusing the 1.2 kb HindIII/EcoR1 fragment from the plasmid pEF-Bos (Mizishuma and Nasgata (1990) NAR 18, 5322), which contains the EF1a promoter, first exon, first intron and a portion of the second exon to the β-globin gene at position –4 relative to the start of transcription of the β-globin gene. The Nco-1/HindIII fragment from the plasmid MLVβ-Plink, containing the polylinker and the β-globin 3' untranslated region was fused to the Nco-1 site of the β-globin gene, which is located across the β-globin start of translation (position +50, relative to the start of transcription), to provide a polylinker and 3' untranslated region for proper mRNA processing.

This entire cassette was to be cloned into the vector pMC1Neo PolyA (Stratagene) pMC1Neo PolyA was first modified to destroy the Nco1 site located in the Neo$^R$ gene and to remove the BamHi, HincII and Sal1 sites located at the 3' end of the Neo$^R$ gene. The EF1α expression cassette was cloned as an HindIII fragment (end repaired) into the Xho1 (end repaired) site in the modified pMC1Neo PolyA plasmid. A vector with the EF1α promoter and the TK promoter (which drives expression of the Neo$^R$ gene) facing in opposite directions was chosen for the expression of CPG2(surface)LNLL; the vector is referred to as pMCEF-Plink. CPG2(surface)LNLL was cloned from pMLVCPG2 (surface) as an Nco1/Xba1 fragment into the Nco1/Xba1 sites of pMCEF-Plink; this plasmid is referred to as pMCEFCPG2(surface)LNLL. As a control plasmid, the lacZ gene was also cloned into the Nco1/Xba1 sites pMCEF-Plink as a Nco1/Xba fragment from the plasmid MLVBlacZ; this is referred to as pMCEFlacZ.

2. Preparation of stable cell lines

Figure 6A:
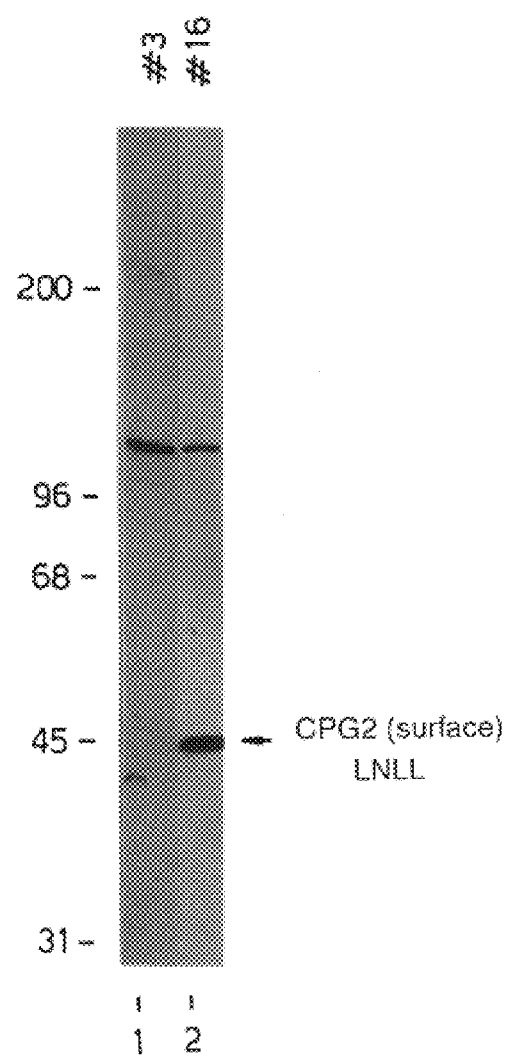
FIG. 6A shows (A) immunoblot analysis. The figure shows constitutive expression of CPG2(surface) LNLL in NIH3T3 cells. The position of migration of CPG2 (surface)LNLL is indicated, as is the position of migration of the standard molecular mass markers (in kDa), to the left of the figure. Lanes 1 and 2 are for cell lines #3 and #16, respectively.
Figure 6B:
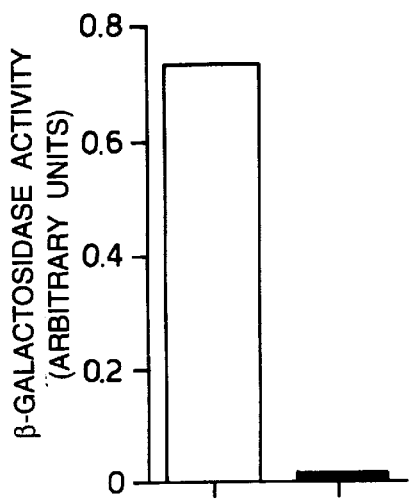
FIG. 6B shows (B) enzymatic activity assay of β-galactosidase.
Figure 6C:
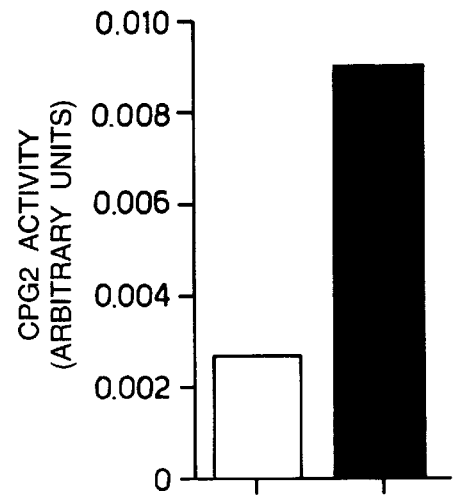
FIG. 6C shows (C) enzymatic activity assay of CPG2. In (B) and (C) the cell extracts from (A) were analysed. The results for NIH3T3 cell line #3 are given in the open bar and for cell line #16 in the solid bar. The activity is expressed as arbitrary values, relative to buffer controls.

Stable cell lines were prepared with NIH3T3 cells to constitutively express CPG2 (surface) LNLL, or as a control the lacZ gene product (β-galactosidase). In order to do this, NIH3T3 cells were transfected with pMCEF-CPG2(surface) LNLL or pMCEFlacZ as described in Comparative Example 1 above, and two days after transfection, the cells were plated at low density into medium containing G418 at 1 mg/ml. Colonies coming from single cells could be observed about two weeks later and these were cloned and grown up individually. The expression of CPG2(surface) was determined by immunoprotein blotting of 30 ml of cell extract (extracted as described in the Comparative Example above) from each of the G418 resistant colonies with the antiserum from the Comparative Example 1 above. The cell line #16 which expresses high levels of CPG2(surface)LNLL (FIG. 6A) and cell line #3, which expresses the β-galactosidase (see below) were selected for further investigation. The expression of CPG2(surface)LNLL and β-galactosidase were verified in the cell lines, by enzymatic assay. For these assays, $1\times10^5$ cells for lines #3 and #16 were plated into 35 mm tissue culture dishes and incubated for 4 days. Cell extracts were prepared (see above) and 5 $\mu$g of protein was subjected to a CMDA degradation assay and a β-galactosidase assay (the CMDA assay is described in the Comparative Example above). For the assay of β-galactosidase activity in cells, 5 $\mu$g of extracted protein was added to 600 $\mu$l of assay buffer (40 mM $Na_2PO_4$, 26.7 mM $NaH_2PO_4$, 6.7 mMKCI, 1 mMMgSO$_4$, 25 mM 2-mercaptoethanol, 50 mM Tris.HCL, 0.06% v/v Triton X-100, 2.2 mM o-nitrophenyl β-D-galactopyranoside) and incubated at 37° C. for 60 min. 250 $\mu$l of 1 M$Na_2CO_3$ was added to the sample and the OD$_{420}$ was measured. The results in FIGS. 6B and 6C show that extracts from line #3 (stippled bars) contain high levels of β-galactosidase activity but no CPG2 activity. The extract from line #16 does not contain any detectable β-galactosidase activity, but does contain detectable levels of CPG2 activity.

Example 3

Figure 7:
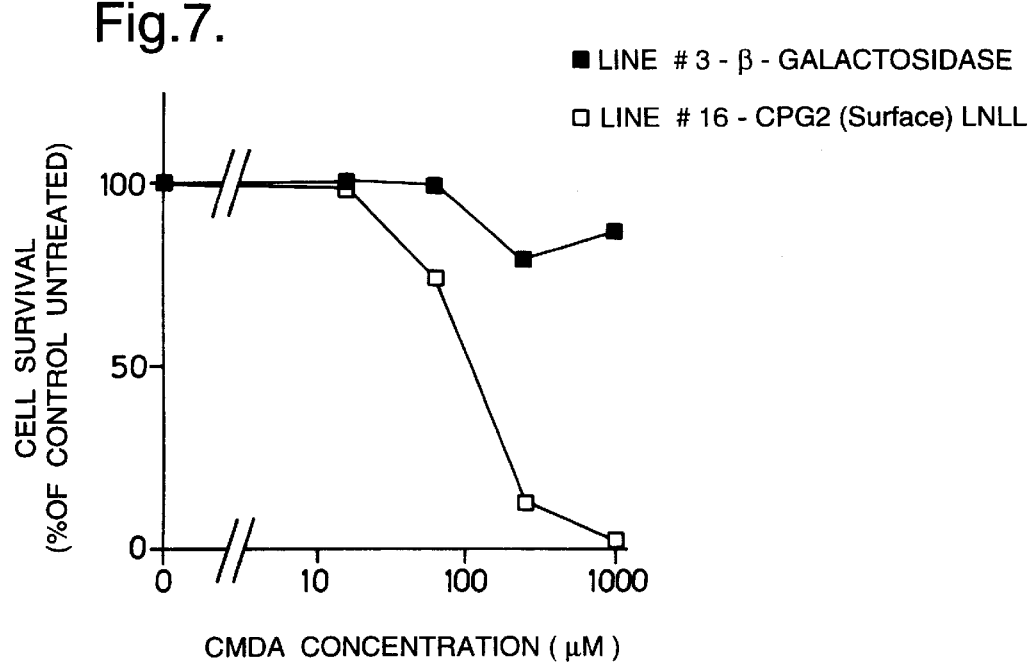
FIG. 7 Sensitivity of NIH3T3 cell lines constitutively expressing CPG2(surface)LNLL or β-galactosidase to the prodrug CMDA.

Cell lines #3 and #16 obtained in Preparative Example 2 were tested for cytotoxicity with the CMDA pro-drug. $1\times10^5$ cells were plated into each well of 24 well dishes, incubated for 40 hours and then treated with increasing concentrations of CMDA at 37° C. for 60 minutes. After a further 6 hour incubation, 10% of the cells were re-plated into 24 well dishes, incubated for a further 5 days and cell survival was determined by [$^3$H]-thymidine incorporation. The results in FIG. 7 show that cell line #3 (filled symbols) is not sensitive to even the highest concentration of CMDA tested, whereas #16 (open symbols) is sensitive in a dose dependent manner, showing an IC50 of –125 $\mu$M.

Example 4

Figure 8:
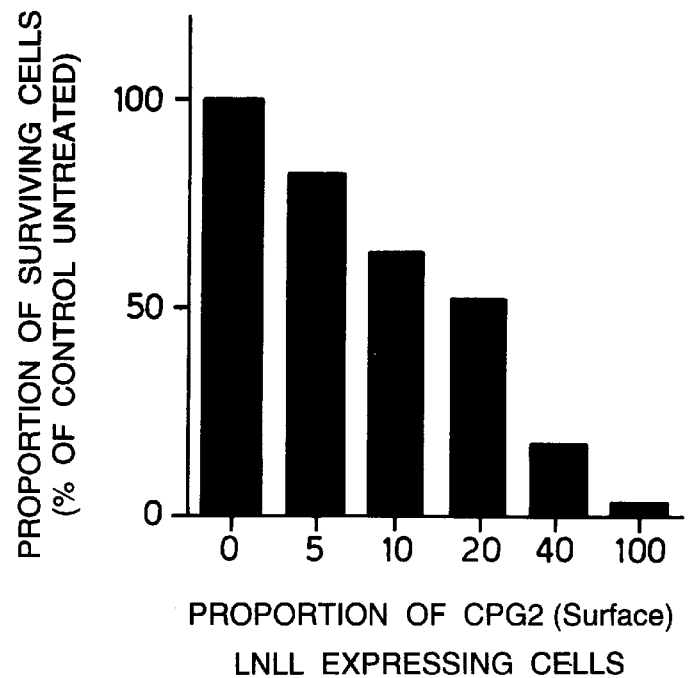
FIG. 8. Bystander effect seen with NIH3T3 cells constitutively expressing CPG2(surface) LNLL and the CMDA prodrug.

The bystander effect was determined by mixing cell lines #3 and #16 obtained in Preparative Example 2 at a variety of concentrations as indicated and a total of 1×10⁵ cells were plated per well in 24 well plates. The cells were incubated and treated as described in Example 3, except that they were treated with either 250 μM or 1000 μM CMDA for 60 minutes as indicated. The cell survival was determined as in Example 3. These results in FIG. 8 show that with these conditions, there is a marginal bystander effect, since with only 40% of the cells expressing CPG2(surface)LNLL, greater than 80% of the cells were killed in the presence of the pro-drug.

PREPARATIVE EXAMPLE 3

In this Example other mutations of the glycosylation sites that would allow increased activity of CPG2 (surface) were prepared. To this end, the viability of making a conserved asparigine to glutamine mutations at codons 222, 264 and 272, the sites shown to be glucosylated, was tested. This was achieved by PCR directed mutagenesis, using the PCR primers:

For codon 222:

1171: 5'>GTG CAG GTC CAA ATC ACC GGC<3' and
1172: 5'>GCC GGT GAT TTG GAC CTG CAC<3'.

For codon 264:

926: >5' CTG CGC TTC CAA TGG ACC ATC<3' and
927: >5' GAT GGT CCA TTG GAA GCG CAG<3'.

For codon 272:

1173: 5'>AAG GCC GGC CAA GTC TCG AAC<3' and
1174: 5'>GTT CGA GAC TTG GCC GGC CTT<3'.

This was done using the experimental protocol described in Example 1.

Figure 9B:
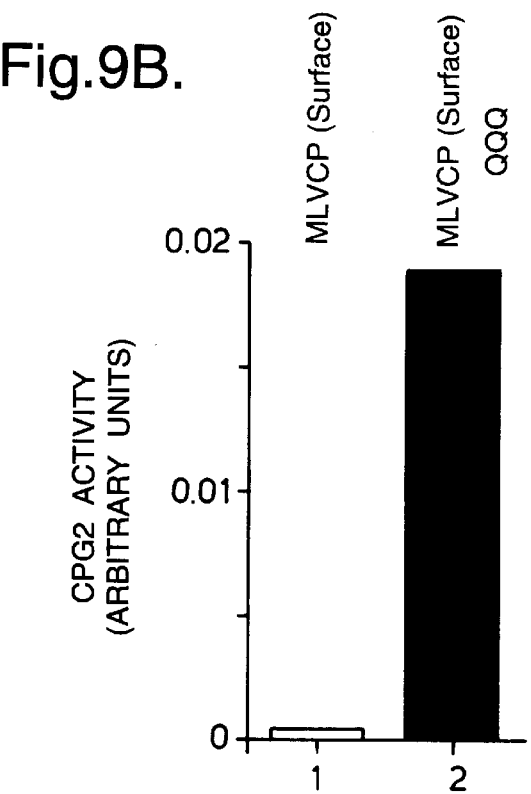
FIG. 9B shows (B) enzymatic activity assay of CPG2. The cell extracts from (A) were analysed. Sample numbers correspond to lane numbers from (A). The activity is expressed as arbitrary values, relative to buffer controls.

The CPG2(surface) containing the codon N222/264/272Q mutations is referred to as CPG2(surface)QQQ and was cloned into MLVβPlink as an NcoI/Xba fragment; this plasmid is called pMLVCPG2(surface)QQQ. In order to test the enzymatic activity of CPG2(surface)QQQ, NIH3T3 cells were transfected with pMLVCPG2(surface) or pMLVCPG2 (surface)QQQ and cell extracts were prepared, these extracts were examined by immunoprotein blotting and for CPG2 enzymatic activity as described in the Comparative Example. The immunoprotein blots show that the CPG2 (surface) QQQ protein (FIG. 9A, lane 2) unlike the CPG2 (surface) protein (FIG. 9A, lane 1) migrates with a mobility consistent with the protein being not glycosylated. From the activity assay data, it can be seen that for similar amounts of activity, the CPG2(surface)QQQ protein (solid bar, FIG. 9B) contains—50 fold higher levels of CPG2 cleaving activity than the CPG2(surface) protein (open bar, FIG. 9B).

Preparation of MDA261B stable cell lines

Figure 10B:
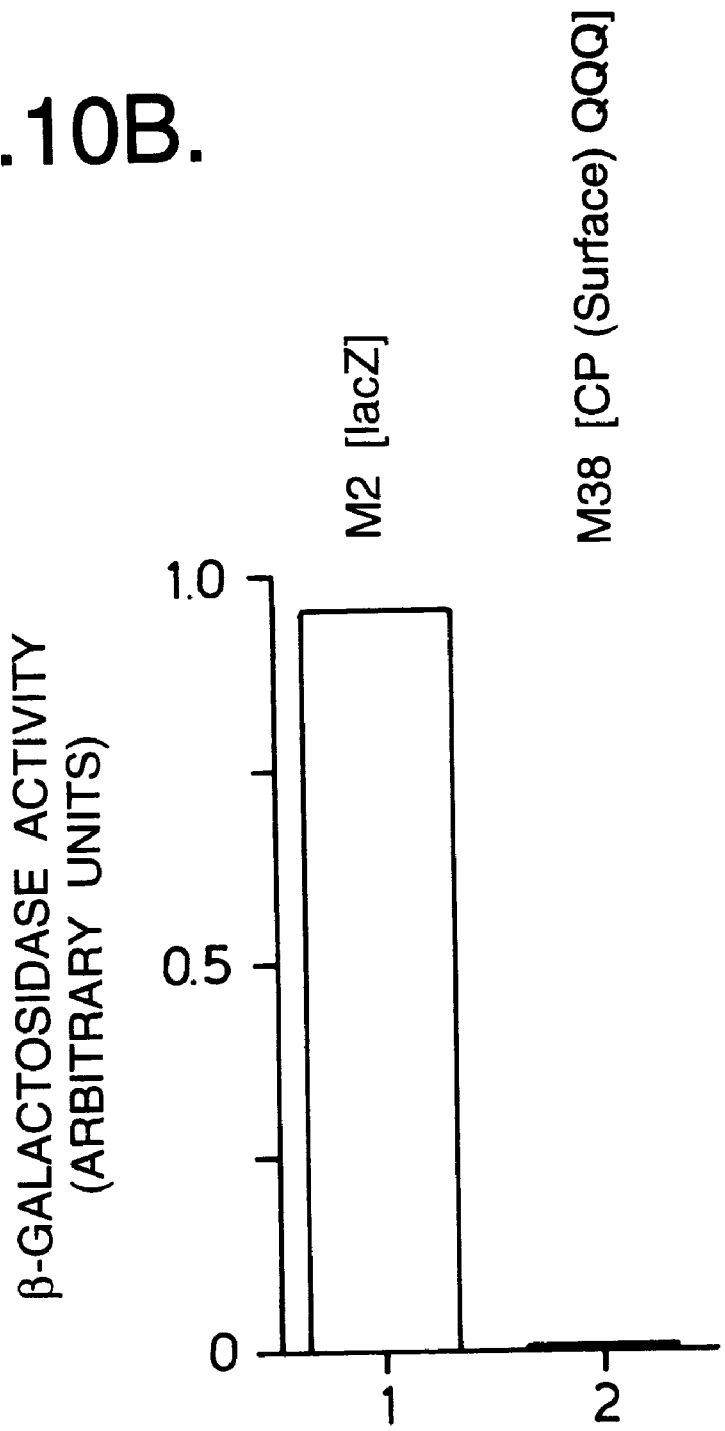
FIG. 10B shows (B) enzymatic activity of β-galactosidase expressed in the MDA MB 361 cell lines M2 and M36. The cell extracts from (A) were analysed. Sample numbers correspond to lane numbers from (A). The activity is expressed as arbitrary values, relative to buffer controls.

Since CPG2(surface)QQQ is more active than CPG2 (surface) MDA261B cell lines were prepared that constitutively express either CPG2(surface)QQQ, or as a control, β-galactosidase. CPG2(surface) QQQ was cloned into pMCEF-Plink as an Nco1/Xba fragment; this plasmid is called pMCEFCPG2(surface)QQQ. MDA361B cells were transfected with either pMCEFCPG2(surface)QQQ, or with pMCEFlacZ according to the protocol described in the Comparative Example and were treated as for the NIH3T3 cells to generate G418 colonies. The G418 resistant colonies were tested for CPG2(surface)QQQ expression by immunoprotein blot analysis, as described for the NIH3T3 cells. From these analyses, two cell lines, M2 which expresses β-galactosidase and M38, which expresses CPG2(surface) QQQ were selected for further testing. Immunoprotein analysis verifies that M38 expresses CPG2(surface)QQQ (FIG. 10A, lane 2), whereas M2 does not (FIG. 10A, lane 1). The expression of β-galactosidase by line M2 was confirmed by enzymatic assay (FIG. 10B, lane 1 contains M2 extract, lane 2 a control extract).

Example 5

Figure 11A:
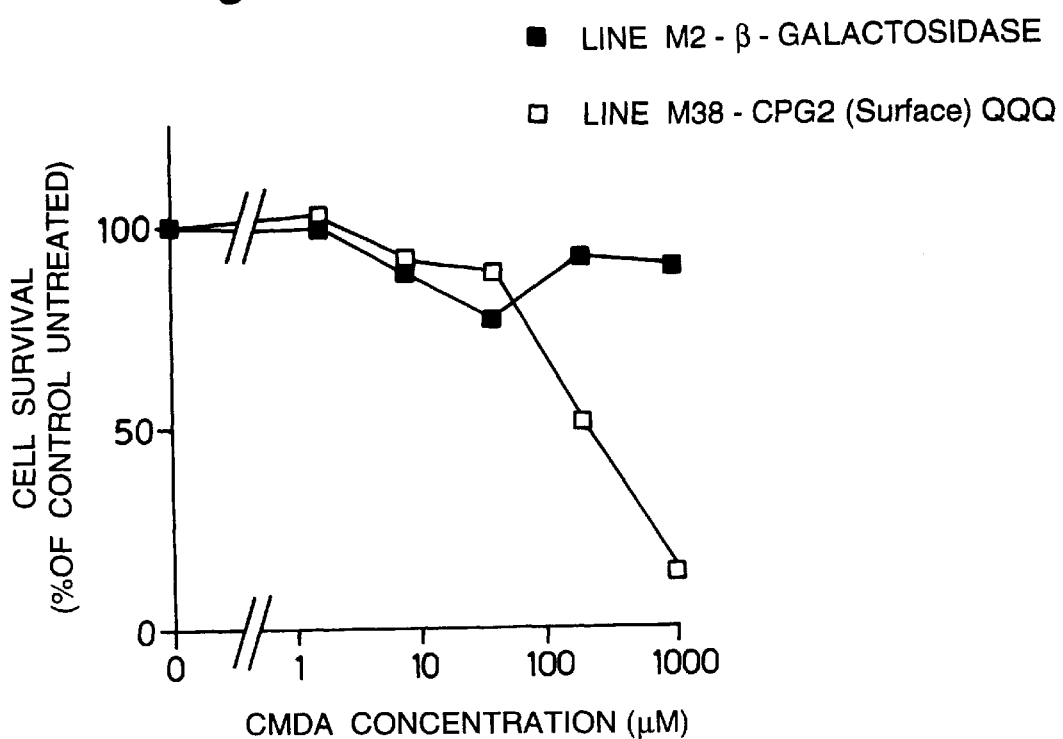
FIG. 11A shows (A) Sensitivity of MDA MB 361 cells constitutively expressing CPG2(surface) QQQ or β-galactosidase to the prodrug CMDA.
Figure 11B:
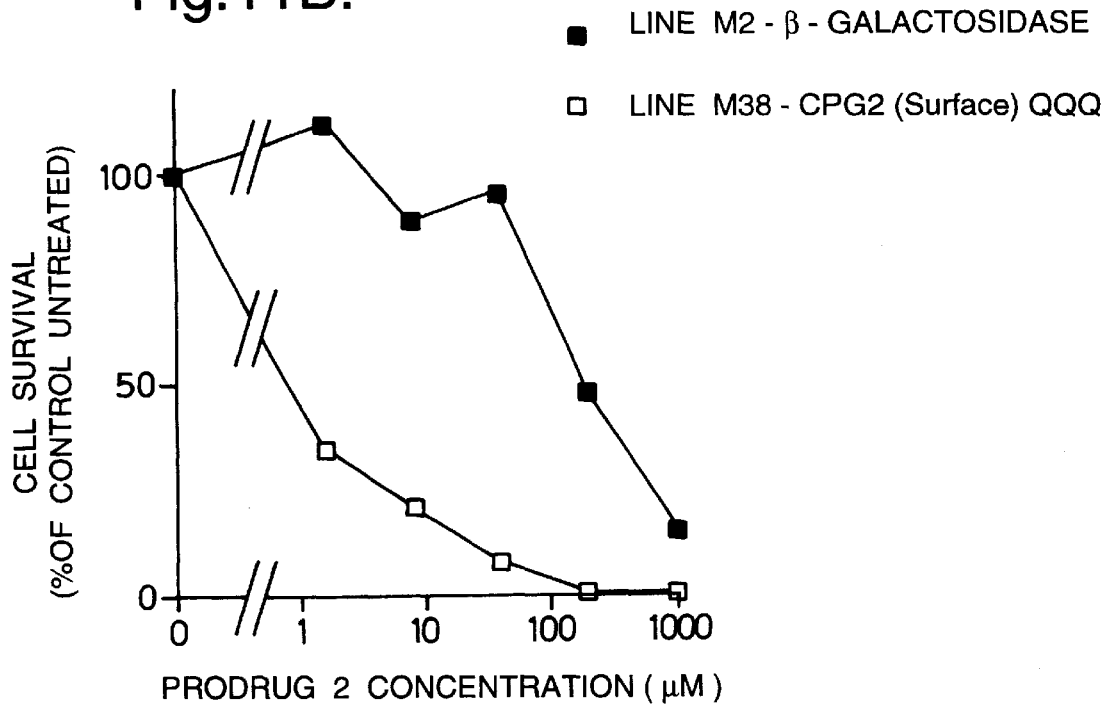
FIG. 11B shows (B) Sensitivity of MDA MB 361 cells constitutively expressing CPG2(surface)QQQ or β-galactosidase to the prodrug 2.

These cell lines were tested for sensitivity to the CMDA prodrug and prodrug 2. 1×10⁵ cells were plated into each well of a 24 well plate. The cells were incubated for 48 hours at 37° C. They were then incubated in increasing concentrations of either CMDA or prodrug 2 for 60 minutes at 37° C., washed twice, returned to medium and incubated for a further 5 days. The viability of the cells was then determined by using [³H]-thymidine incorporation. The results show that the cell line expressing CPG2(surface)QQQ (line M38, FIG. 11A and 11B, open symbols) was more sensitive to both prodrugs than the line expressing β-galactosidase (line M2, FIG. 11A and 11B, closed symbols).

For prodrug CMDA, it was not possible to judge how much more sensitive M38 was than M2 as M2 did not show any sensitivity to the prodrug, even at the highest concentration tested. However, with prodrug 2, the differential was substantial, the M38 cells being of the order of 200 fold more sensitive to the prodrug than the M2 cells.

Example 6

Figure 12:
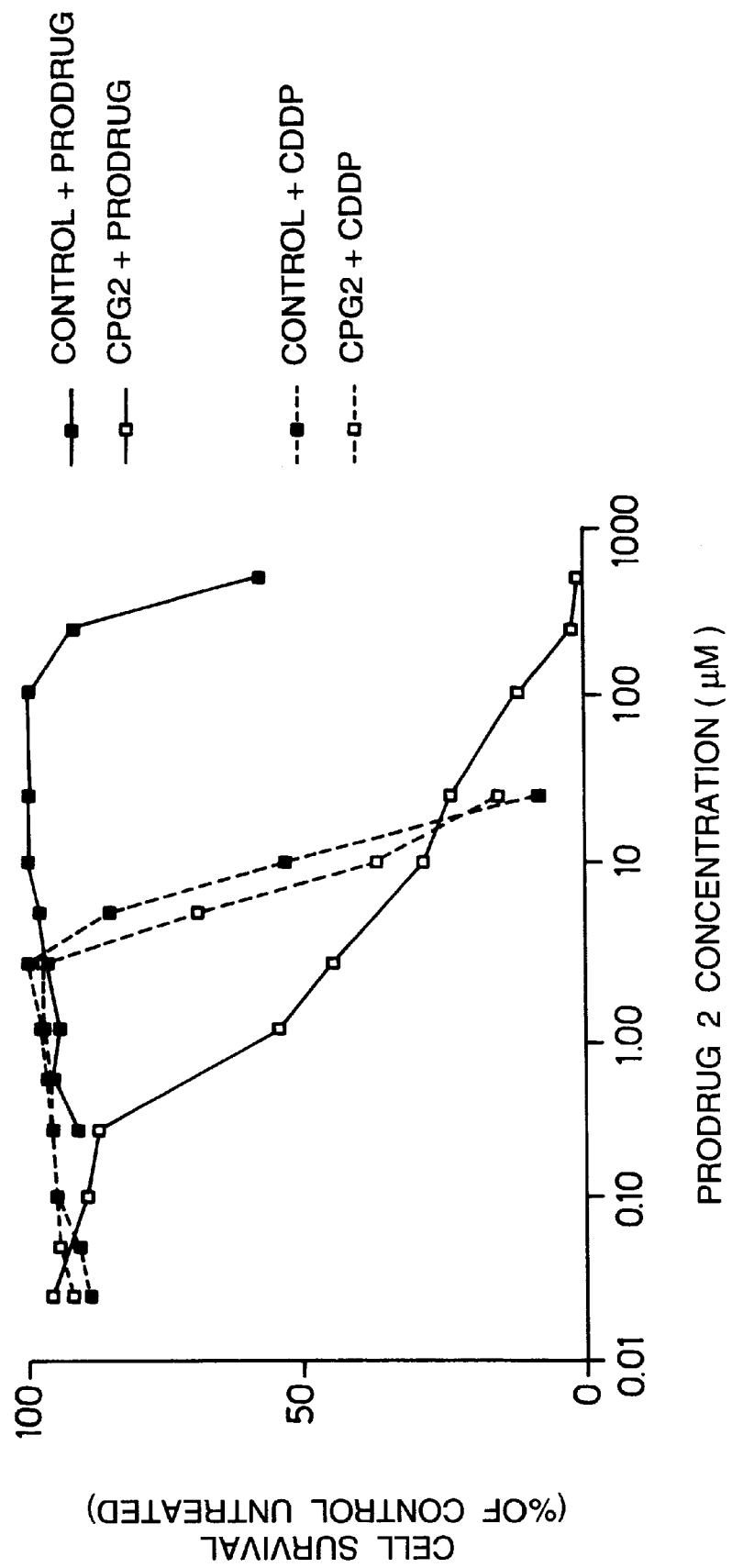
FIG. 12. Sensitivity of MDA MB 361 cells constitutively expressing CPG2, to the prodrug 2—sulphorhodamine assay.
Figure 13:
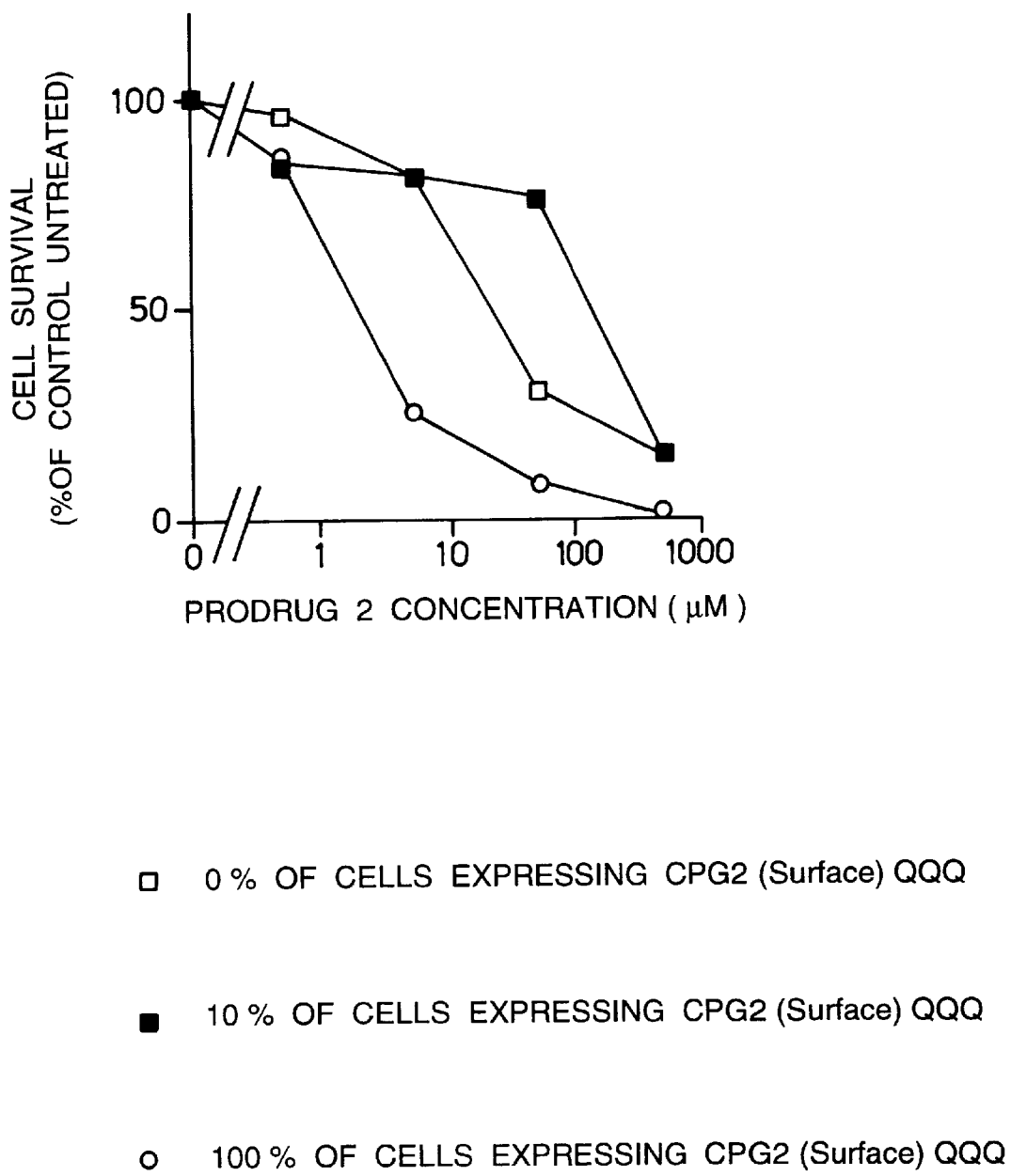
FIG. 13. Bystander effect seen in the MDA MB 361 cell lines constitutively expressing CPG2(surface)QQQ with prodrug 2.

Prodrug 2 was also assayed (FIG. 12) in the MDA MB361 transfected cells obtained in Preparative Example 3 using a sulphorhodamine B cytotoxicity assay which was conducted by plating 5000 cells per well in a 96-well microtitre dish. The cells were plated in 160 μl of DMEM medium. After incubation over night the drug or appropriate controls made up in DMEM containing 5% serum was added to the wells in a 40 μl volume. The cells were incubated for 4 days under standard conditions. Following this the medium was removed and the cells treated with ice-cold 10% TCA (trichloroacetic acid) on ice for about 30 minutes. The TCA was removed and the cells rinsed for adding 18 μl of 0.4% sulphorhodamine B (SRB) which was left to stain the cells for 10 minutes. Following staining the cells were rinsed in TCA and air dried before addition of 18 μl of 10 mM TRIS and cell viability was then read. Cisplatin (CDDP) was used as a control to ensure that each line was equally susceptible (i.e. to check that the CPG2 expressing line had not been rendered more sensitive to cell-killing agents). There was not found to be any difference between the susceptibility to CDDP for the CPG2—expressing line compared to the control I2C-Z line. (see FIG. 12)

Example 7

In order to examine the bystander effect with the MDA MB 361 cells constitutively expressing CPG2(surface) QQQ, the M38 cell line, the M2 cell line, or a 1:10 mixture of M38: M2 cells were plated (1×10⁴ cells) into the wells of a 24 well plate, and incubated for 48 hours. The cells were then treated with varying concentrations of prodrug 2 for 60 min, washed twice with fresh medium and incubated in fresh medium for 5 days. The survival of the cells was then determined by [³H-methyl] thymidine incorporation. The results show the M38 cell line (IC50~1 μM) is ~200 fold more sensitive to the prodrug than the M2 cell line (IC50~200 μM). However, when these two cell lines are mixed at a ratio of 1:10, the IC50 was reduced ~10 fold (~20 μM), despite the fact that only 10% of the cells were expressing CPG2(surface)QQQ and demonstrating a substantial bystander effect.

We claim:

1. A product comprising two components for use in association with one another comprising:
   (a) a vector comprising a eukaryotic promoter operably linked to a gene, said gene comprising a nucleic acid sequence encoding a bacterial carboxypeptidase G which has been altered at one or more glycosylation sites to prevent glycosylation at said site or sites together with a signal sequence, wherein upon expression of said gene in a eukaryotic tumor cell said signal sequence directs and tethers said bacterial carboxypeptidase to the plasma membrane of said tumor cell; and
   (b) a prodrug which can be converted into an active drug by said bacterial carboxypeptidase G.

2. A product according to claim 1 wherein the bacterial carboxypeptidase G is carboxypeptidase CPG2.

3. A product according to claim 1 wherein the prodrug is a nitrogen mustard prodrug.

4. A product according to claim 1 wherein the signal sequence comprises a nucleic acid sequence encoding a signal peptide of a transmembrane receptor kinase.

5. A product according to claim 1 wherein said promoter is expressed in a tissue restricted manner.

6. A product according to claim 5 wherein the promoter is a c-erbB2 promoter.

7. A product according to claim 2 wherein one or more of the residues Asn 222, Asn 264 and Asn 272 of the CPG2 have been substituted.

8. A product according to claim 2 wherein the residues 222 and 272 have been altered to glutamine and residue 266 altered to leucine.

9. A bacterial carboxypeptidase G which comprises a substitution, deletion or insertion at one or more glycosylation sites so as to prevent glycosylation at said site while retaining carboxypeptidase activity.

10. A carboxypeptidase according to claim 9 which is CPG2.

11. A carboxypeptidase according to claim 10 wherein residues 222 and 272 have been altered to glutamine and residue 266 has been altered to leucine.

12. A carboxypeptidase according to claim 10 in which one or more of the residues Asn 222, Asn 264 and Asn 272 have been substituted.

13. A vector comprising a nucleic acid sequence encoding the bacterial carboxypeptidase G of claim 9.

14. A vector according to claim 13 which further comprises a signal sequence capable of directing expression of the carboxypeptidase to the surface of a mammalian cell.

15. A vector according to claim 14 the signal sequence is a signal peptide of a transmembrane receptor kinase.

16. A method of treating a tumor in a patient in need of treatment which method comprises administering to said patient an effective amount of a vector comprising a eukaryotic promoter operably linked to a gene, said gene comprising a nucleic acid sequence encoding a bacterial carboxypeptidase G which has been altered at one or more glycosylation sites to prevent glycosylation at said site or sites, together with a signal sequence, wherein upon expression of said gene in a eukaryotic tumor cell said signal sequence directs and tethers said bacterial carboxypeptidase G to the plasma membrane of said tumor cell, and, a prodrug which can be converted into an active drug by said bacterial carboxypeptidase G to provide a tumoricidal effect on said tumor.

17. The method of claim 16 wherein said tumor is a breast cancer.

18. The method of claim 16 wherein the prodrug is a nitrogen mustard prodrug.

19. A method of treating a breast tumor in a patient in need of treatment which method comprises administering to said patient an effective amount of a vector comprising a eukaryotic promoter operably linked to a gene, said gene comprising a nucleic acid sequence encoding a bacterial carboxypeptidase G which has been altered at one or more glycosylation sites to prevent glycosylation at said site or sites, together with a signal sequence, wherein upon expression of said gene in a eukaryotic tumor cell said signal sequence directs and tethers said bacterial carboxypeptidase G to the plasma membrane of said tumor cell, and, a nitrogen mustard prodrug which can be converted into an active drug by said bacterial carboxypeptidase G, said active drug having a tumoricidal effect on said breast tumor.

20. In a method of treatment of a tumor cell by gene-directed enzyme-prodrug therapy by delivering to a patient in need of treatment a gene which is expressed in the tumor to provide a gene product, and a prodrug which is converted to an active drug by said gene product, the improvement comprising expressing a gene which encodes a gene product comprising a bacterial carboxypeptidase G which has been altered at one or more glycosylation sites to prevent glycosylation at said site or sites, which gene product is transported to and tethered to the plasma membrane of the tumor cell and said active drug provides a tumoricidal effect on said tumor cell.

21. A method of expressing a bacterial carboxypeptidase G in a eukaryotic cell, said bacterial carboxypeptidase G comprising a substitution deletion or insertion at one or more glycosylation sites so as to prevent glycosylation at said site while retaining carboxypeptidase activity, said method comprising culturing a eukaryotic cell which has been transformed with a vector according to claim 13 under conditions whereby said bacterial carboxypeptidase is expressed.

22. The method according to claim 21 further comprising transforming said eukaryotic cell into said vector prior to said culturing.

23. A vector comprising a eukaryotic promoter operably linked to a gene, said gene comprising a nucleic acid sequence encoding a bacterial carboxypeptidase G together with a signal sequence, wherein upon expression of said gene in a eukaryotic tumor cell said signal sequence directs and tethers said bacterial carboxypeptidase G to the plasma membrane of said tumor cell.

* * * * *

SEQUENCE LISTING (1) GENERAL INFORMATION:

(iii) NUMBER OF SEQUENCES: 27

(2) INFORMATION FOR SEQ ID NO: 1:

(i) SEQUENCE CHARACTERISTICS:
      (A) LENGTH: 2048 base pairs
      (B) TYPE: nucleic acid
      (C) STRANDEDNESS: double
      (D) TOPOLOGY: circular (ii) MOLECULE TYPE: DNA (genomic)

(xi) SEQUENCE DESCRIPTION: SEQ ID NO: 1:

```
ATCATGGATC CACGCACTGA AGGCGCGCGG CAAGACGCGC GGCGTGGCGA CGCTGTGCAT      60

CGGCGGGGGC GAAGGCACCG CAGTGGCACT CGAATTGCTA TAAGAACCAT GGCTGGGGAC     120

GCCCGACAAC AGGCGTCCAC CAGCTTTTTT CATTCCGACA ACCCGAACGA ACAATGCGTA     180

GAGCAGGAGA TTCC ATG CGC CCA TCC ATC CAC CGC ACA GCC ATC GCC GCC      230
             Met Arg Pro Ser Ile His Arg Thr Ala Ile Ala Ala
              1               5                  10

GTG CTG GCC ACC GCC TTC GTG GCG GGC ACC GCC CTG GCC CAG AAG CGC      278
Val Leu Ala Thr Ala Phe Val Ala Gly Thr Ala Leu Ala Gln Lys Arg
            15                  20                  25

GAC AAC GTG CTG TTC CAG GCA GCT ACC GAC GAG CAG CCG GCC GTG ATC      326
Asp Asn Val Leu Phe Gln Ala Ala Thr Asp Glu Gln Pro Ala Val Ile
 30                  35                  40

AAG ACG CTG GAG AAG CTG GTC AAC ATC GAG ACC GGC ACC GGT GAC GCC      374
Lys Thr Leu Glu Lys Leu Val Asn Ile Glu Thr Gly Thr Gly Asp Ala
 45                  50                  55                  60

GAG GGC ATC GCC GCT GCG GGC AAC TTC CTC GAG GCC GAG CTC AAG AAC      422
Glu Gly Ile Ala Ala Ala Gly Asn Phe Leu Glu Ala Glu Leu Lys Asn
                 65                  70                  75

CTC GGC TTC ACG GTC ACG CGA AGC AAG TCG GCC GGC CTG GTG GTG GGC      470
Leu Gly Phe Thr Val Thr Arg Ser Lys Ser Ala Gly Leu Val Val Gly
             80                  85                  90

GAC AAC ATC GTG GGC AAG ATC AAG GGC CGC GGC GGC AAG AAC CTG CTG      518
Asp Asn Ile Val Gly Lys Ile Lys Gly Arg Gly Gly Lys Asn Leu Leu
         95                  100                 105

CTG ATG TCG CAC ATG GAC ACC GTC TAC CTC AAG GGC ATT CTC GCG AAG      566
Leu Met Ser His Met Asp Thr Val Tyr Leu Lys Gly Ile Leu Ala Lys
     110                 115                 120

GCC CCG TTC CGC GTC GAA GGC GAC AAG GCC TAC GGC CCG GGC ATC GCC      614
Ala Pro Phe Arg Val Glu Gly Asp Lys Ala Tyr Gly Pro Gly Ile Ala
125                 130                 135                 140

GAC GAC AAG GGC GGC AAC GCG GTC ATC CTG CAC ACG CTC AAG CTG CTG      662
Asp Asp Lys Gly Gly Asn Ala Val Ile Leu His Thr Leu Lys Leu Leu
                145                 150                 155

AAG GAA TAC GGC GTG CGC GAC TAC GGC ACC ATC ACC GTG CTG TTC AAC      710
Lys Glu Tyr Gly Val Arg Asp Tyr Gly Thr Ile Thr Val Leu Phe Asn
                160                 165                 170

ACC GAC GAG GAA AAG GGT TCC TTC GGC TCG CGC GAC CTG ATC CAG GAA      758
Thr Asp Glu Glu Lys Gly Ser Phe Gly Ser Arg Asp Leu Ile Gln Glu
            175                 180                 185

GAA GCC AAG CTG GCC GAC TAC GTG CTC TCC TTC GAG CCC ACC AGC GCA      806
Glu Ala Lys Leu Ala Asp Tyr Val Leu Ser Phe Glu Pro Thr Ser Ala
        190                 195                 200

GGC GAC GAA AAA CTC TCG CTG GGC ACC TCG GGC ATC GCC TAC GTG CAG      854
```

```
Gly Asp Glu Lys Leu Ser Leu Gly Thr Ser Gly Ile Ala Tyr Val Gln
205                 210                 215                 220

GTC AAC ATC ACC GGC AAG GCC TCG CAT GCC GGC GCC GCG CCC GAG CTG        902
Val Asn Ile Thr Gly Lys Ala Ser His Ala Gly Ala Ala Pro Glu Leu
                225                 230                 235

GGC GTG AAC GCG CTG GTC GAG GCT TCC GAC CTC GTG CTG CGC ACG ATG        950
Gly Val Asn Ala Leu Val Glu Ala Ser Asp Leu Val Leu Arg Thr Met
            240                 245                 250

AAC ATC GAC GAC AAG GCG AAG AAC CTG CGC TTC AAC TGG ACC ATC GCC        998
Asn Ile Asp Asp Lys Ala Lys Asn Leu Arg Phe Asn Trp Thr Ile Ala
                255                 260                 265

AAG GCC GGC AAC GTC TCG AAC ATC ATC CCC GCC AGC GCC ACG CTG AAC       1046
Lys Ala Gly Asn Val Ser Asn Ile Ile Pro Ala Ser Ala Thr Leu Asn
        270                 275                 280

GCC GAC GTG CGC TAC GCG CGC AAC GAG GAC TTC GAC GCC GCC ATG AAG       1094
Ala Asp Val Arg Tyr Ala Arg Asn Glu Asp Phe Asp Ala Ala Met Lys
285                 290                 295                 300

ACG CTG GAA GAG CGC GCG CAG CAG AAG AAG CTG CCC GAG GCC GAC GTG       1142
Thr Leu Glu Glu Arg Ala Gln Gln Lys Lys Leu Pro Glu Ala Asp Val
                305                 310                 315

AAG GTG ATC GTC ACG CGC GGC CGC CCG GCC TTC AAT GCC GGC GAA GGC       1190
Lys Val Ile Val Thr Arg Gly Arg Pro Ala Phe Asn Ala Gly Glu Gly
                320                 325                 330

GGC AAG AAG CTG GTC GAC AAG GCG GTG GCC TAC TAC AAG GAA GCC GGC       1238
Gly Lys Lys Leu Val Asp Lys Ala Val Ala Tyr Tyr Lys Glu Ala Gly
            335                 340                 345

GGC ACG CTG GGC GTG GAA GAG CGC ACC GGC GGC GGC ACC GAC GCG GCC       1286
Gly Thr Leu Gly Val Glu Glu Arg Thr Gly Gly Gly Thr Asp Ala Ala
350                 355                 360

TAC GCC GCG CTC TCA GGC AAG CCA GTG ATC GAG AGC CTG GGC CTG CCG       1334
Tyr Ala Ala Leu Ser Gly Lys Pro Val Ile Glu Ser Leu Gly Leu Pro
365                 370                 375                 380

GGC TTC GGC TAC CAC AGC GAC AAG GCC GAG TAC GTG GAC ATC AGC GCG       1382
Gly Phe Gly Tyr His Ser Asp Lys Ala Glu Tyr Val Asp Ile Ser Ala
                385                 390                 395

ATT CCG CGC CGC CTG TAC ATG GCT GCG CGC CTG ATC ATG GAT CTG GGC       1430
Ile Pro Arg Arg Leu Tyr Met Ala Ala Arg Leu Ile Met Asp Leu Gly
                400                 405                 410

GCC GGC AAG T GAATGCTGCC CCCCGGCTTT TCACTCGCGT TGCTCGTGTA             1480
Ala Gly Lys
        415

ACTCCACCCC CCGAGGGGGA GGCGCGGTCC GCCTTGGGGC GGCCCGGCGG CGACCGCCTC     1540

GTCACATAGA AGGAACTGCC ATGTTGTTGA CAGCAGACCA GGAAGCCATC CGCGACGCGG     1600

TGCGCGACTT CTCGCAAGCC GAACTCTGGC CCAACGCCGC GAATGGGGAC CGCGAGCACA     1660

GCTTTCCCAA GAGCCCACCA GGCCGTCGGC TGGCGTACGC AGTCTGCGTG CCCGAGGAGC     1720

ATGGCGGCGC CGGCCTCGAC TACCTCACCT CGCGCTGGTG CTGGAGGAGA TCGCGGCCGG     1780

CGACGGCGGC ACCAGCACCG CCATCAGCGT GACCAACTGC CCCGTCAACG CCATCCTCAT     1840

GCGCTACGGC AACGCGCAGC AGAAGAAGCA GTGGCTCGAG CCGCTGGCGC AGGGCCGGAT     1900

GCTCGGCGCC TTCTGCCTGA CCGAGCCGCA GGCCGGCAGC GATGCATCGA GCCTGCGCAC     1960

CACGGCGCGC AAGGACGGCG ACGGCTACGT GATCGACGGC GTGAAGCAGT TCATCACCAG     2020

CGGCAAGAAC GGCCAGGTGG CGGGATCC                                       2048

(2) INFORMATION FOR SEQ ID NO:2:

(i) SEQUENCE CHARACTERISTICS:
```

(A) LENGTH: 81 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:2:

ATGGAGCTGG CGGCCTTGTC CCGCTGGGGG CTCCTCCTCG CCCTCTTGCC CCCCGGAGCC    60

GCGAGCACCC AAGTGTGCAC C    81

(2) INFORMATION FOR SEQ ID NO:3:

(i) SEQUENCE CHARACTERISTICS:
        (A) LENGTH: 153 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

GACCTGGATG ACAAGGGCTG CCCCGCCGAG CAGAGAGCCA GCCCTCTGAC GTCCATCGTC    60

TCTGCGGTGG TTGGCATTCT CCTGGTCGTG GTCTTGGGGG TGGTCTTTGG GATCCTCATC   120

AAGCGACGGC AGCAGAAGAT CCGGAAGTAC ACG   153

(2) INFORMATION FOR SEQ ID NO:4:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

GCTTACAATT GCTTCTGACA C    21

(2) INFORMATION FOR SEQ ID NO:5:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

CGCGGATCCG GTGCACACTT GGGTGCTC    28

(2) INFORMATION FOR SEQ ID NO:6:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

CGCGGATCCG CCCTGGCCCA GAAGCGC    27

(2) INFORMATION FOR SEQ ID NO:7:

(i) SEQUENCE CHARACTERISTICS:
    (A) LENGTH: 27 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:7:

CGCGAATTCC TTGCCGGCGC CCAGATC                                       27

(2) INFORMATION FOR SEQ ID NO:8:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

GCGGAATTCG ACCTGGATGA CAAGGGC                                       27

(2) INFORMATION FOR SEQ ID NO:9:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

CGCATCGATC GTGTACTTCC GGATCCT                                       27

(2) INFORMATION FOR SEQ ID NO:10:

(i) SEQUENCE CHARACTERISTICS:
        (A) LENGTH: 816 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

CATGGAGCTG GCGGCCTTGT CCCGCTGGGG GCTCCTCCTC GCCCTCTTGC CCCCCGGAGC    60

CGCGAGCACC CAAGTGTGCA CCCGACCTGG ATGACAAGGG CTGCCCCGCC GAGCAGAGAG   120

CCAGCCCTCT GACGTCCATC GTCTCTGCGG TGGTTGGCAT TCTCCTGGTC GTGGTCTTGG   180

GGGTGGTCTT TGGGATCCTC ATCAAGCGAC GGCAGCAGAA GATCCGGAAG TACACGGCTT   240

ACAATTGCTT CTGACACCGC GGATCCGGTG CACACTTGGG TGCTCCGCGG ATCCGCCCTG   300

GCCCAGAAGC GCCGCGAATT CCTTGCCGGC GCCCAGATCG CGGAATTCGA CCTGGATGAC   360

AAGGGCCGCA TCGATCGTGT ACTTCCGGAT CCTCGATGAG CAGAAGCTGA TATCCGAGGA   420

GGACCTGAAC TAGTTCAGGT CCTCCTCGGA TATCAGCTTC TGCTCATCCG GCATGCGAGG   480

CCTTGCCGGT GATGAGGACC TGCACCGAAG GCCCCGTTCC GCGCTGCGCT TCCTCTGGAC   540

CATCGATGGT CCAGAGGAAG CGCAGTGCAG GTCAACATCA CCGTTCTTGC CGCCTTCGCC   600

GGCAAGGCCG GCCTCGTCTC GAACGTTCGA GACGAGGCCG GCCTTTCCAA CTGGGTCATC   660

GCCAAGCTTG GCGATGACCC AGTTGAACGT GCAGGTCCAA ATCACCGGCG CCGGTGATTT   720

```
GGACCTGCAC CCTGCGCTTC CAATGGACCA TCGATGGTCC ATTGGAAGCG CAGCAAGGCC      780

GGCCAAGTCT CGAACGTTCG AGACTTGGCC GGCCTT                                816

(2) INFORMATION FOR SEQ ID NO:11:

(i) SEQUENCE CHARACTERISTICS:
         (A) LENGTH: 38 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:11:

CTAGTTCAGG TCCTCCTCGG ATATCAGCTT CTGCTCAT                               38

(2) INFORMATION FOR SEQ ID NO:12:

(i) SEQUENCE CHARACTERISTICS:
         (A) LENGTH: 38 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:12:

CCGGCATGCG AGGCCTTGCC GGTGATGAGG ACCTGCAC                               38

(2) INFORMATION FOR SEQ ID NO:13:

(i) SEQUENCE CHARACTERISTICS:
         (A) LENGTH: 18 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:13:

CGAAGGCCCC GTTCCGCG                                                    18

(2) INFORMATION FOR SEQ ID NO:14:

(i) SEQUENCE CHARACTERISTICS:
         (A) LENGTH: 21 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:14:

CTGCGCTTCC TCTGGACCAT C                                                21

(2) INFORMATION FOR SEQ ID NO:15:

(i) SEQUENCE CHARACTERISTICS:
         (A) LENGTH: 21 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:15:

GATGGTCCAG AGGAAGCGCA G                                                21
```

(2) INFORMATION FOR SEQ ID NO:16:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

TGCAGGTCAA CATCACCG                                            18

(2) INFORMATION FOR SEQ ID NO:17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

TTCTTGCCGC CTTCGCCGGC                                          20

(2) INFORMATION FOR SEQ ID NO:18:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:18:

AAGGCCGGCC TCGTCTCGAA C                                        21

(2) INFORMATION FOR SEQ ID NO:19:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

GTTCGAGACG AGGCCGGCCT T                                        21

(2) INFORMATION FOR SEQ ID NO:20:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:20:

TCCAACTGGG TCATCGCCAA G                                        21

(2) INFORMATION FOR SEQ ID NO:21:

(i) SEQUENCE CHARACTERISTICS:
           (A) LENGTH: 21 base pairs
           (B) TYPE: nucleic acid
           (C) STRANDEDNESS: single
           (D) TOPOLOGY: linear (ii) MOLECULE TYPE: cDNA (xi) SEQUENCE DESCRIPTION: SEQ ID NO:21:

CTTGGCGATG ACCCAGTTGA A                                              21

(2) INFORMATION FOR SEQ ID NO:22:

(i) SEQUENCE CHARACTERISTICS:
           (A) LENGTH: 21 base pairs
           (B) TYPE: nucleic acid
           (C) STRANDEDNESS: single
           (D) TOPOLOGY: linear (ii) MOLECULE TYPE: cDNA (xi) SEQUENCE DESCRIPTION: SEQ ID NO:22:

GTGCAGGTCC AAATCACCGG C                                              21

(2) INFORMATION FOR SEQ ID NO:23:

(i) SEQUENCE CHARACTERISTICS:
           (A) LENGTH: 21 base pairs
           (B) TYPE: nucleic acid
           (C) STRANDEDNESS: single
           (D) TOPOLOGY: linear (ii) MOLECULE TYPE: cDNA (xi) SEQUENCE DESCRIPTION: SEQ ID NO:23:

GCCGGTGATT TGGACCTGCA C                                              21

(2) INFORMATION FOR SEQ ID NO:24:

(i) SEQUENCE CHARACTERISTICS:
           (A) LENGTH: 21 base pairs
           (B) TYPE: nucleic acid
           (C) STRANDEDNESS: single
           (D) TOPOLOGY: linear (ii) MOLECULE TYPE: cDNA (xi) SEQUENCE DESCRIPTION: SEQ ID NO:24:

CTGCGCTTCC AATGGACCAT C                                              21

(2) INFORMATION FOR SEQ ID NO:25:

(i) SEQUENCE CHARACTERISTICS:
           (A) LENGTH: 21 base pairs
           (B) TYPE: nucleic acid
           (C) STRANDEDNESS: single
           (D) TOPOLOGY: linear (ii) MOLECULE TYPE: cDNA (xi) SEQUENCE DESCRIPTION: SEQ ID NO:25:

GATGGTCCAT TGGAAGCGCA G                                              21

(2) INFORMATION FOR SEQ ID NO:26:

(i) SEQUENCE CHARACTERISTICS:
           (A) LENGTH: 21 base pairs
           (B) TYPE: nucleic acid
           (C) STRANDEDNESS: single

```
                    -continued (D) TOPOLOGY: linear (ii) MOLECULE TYPE: cDNA (xi) SEQUENCE DESCRIPTION: SEQ ID NO:26:

AAGGCCGGCC AAGTCTCGAA C                                      21

(2) INFORMATION FOR SEQ ID NO:27:

(i) SEQUENCE CHARACTERISTICS:
         (A) LENGTH: 21 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:27:

GTTCGAGACT TGGCCGGCCT T                                      21
```